United States Patent
Ban et al.

(10) Patent No.: US 12,398,149 B2
(45) Date of Patent: Aug. 26, 2025

(54) DIHYDROCHROMENE DERIVATIVES

(71) Applicant: Sumitomo Pharma Co., Ltd., Osaka (JP)

(72) Inventors: Hitoshi Ban, Osaka (JP); Seiji Kamioka, Osaka (JP); Yusuke Sawayama, Osaka (JP); Miki Hashizume, Osaka (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 66 days.

(21) Appl. No.: 18/187,124

(22) Filed: Mar. 21, 2023

(65) Prior Publication Data

US 2023/0219970 A1 Jul. 13, 2023

Related U.S. Application Data

(63) Continuation of application No. 16/944,482, filed on Jul. 31, 2020, now Pat. No. 11,639,357, which is a continuation of application No. 16/808,246, filed on Mar. 3, 2020, now Pat. No. 10,807,993, which is a continuation of application No. PCT/JP2019/011439, filed on Mar. 19, 2019.

(30) Foreign Application Priority Data

Mar. 20, 2018 (JP) .................... 2018-052971

(51) Int. Cl.
| | | |
|---|---|---|
| C07D 491/20 | (2006.01) | |
| A61K 31/436 | (2006.01) | |
| A61K 31/438 | (2006.01) | |
| A61P 35/00 | (2006.01) | |

(52) U.S. Cl.
CPC .......... *C07D 491/20* (2013.01); *A61K 31/436* (2013.01); *A61K 31/438* (2013.01); *A61P 35/00* (2018.01)

(58) Field of Classification Search
None
See application file for complete search history.

(56) References Cited

U.S. PATENT DOCUMENTS

| | | |
|---|---|---|
| 10,807,993 B2 | 10/2020 | Ban |
| 2008/0255149 A1 | 10/2008 | Dobler et al. |
| 2011/0112180 A1 | 5/2011 | Jiang et al. |
| 2017/0166552 A1 | 6/2017 | Ban et al. |
| 2018/0127386 A1 | 5/2018 | Lee |

FOREIGN PATENT DOCUMENTS

| | | |
|---|---|---|
| JP | 2009-510073 | 3/2009 |
| JP | 2010-539095 | 12/2010 |
| WO | 2016-208591 | 12/2016 |
| WO | WO 2016/208592 A1 | 12/2016 |
| WO | WO 2017/146128 A1 | 8/2017 |

OTHER PUBLICATIONS

Ahmad et. al. ((2018), Identification of natural inhibitors against Acinetobacter baumannii D-alanine-D-alanine ligase enzyme A multi-spectrum in silico approach, Journal of Molecular Liquids, 262, 460-475 (Year: 2018).*
International Search Report mailing date of Jun. 18, 2019, Application No. PCT/JP2019/011439.

(Continued)

*Primary Examiner* — Juliet C Switzer
*Assistant Examiner* — Dawanna Shar-Day White
(74) *Attorney, Agent, or Firm* — Oblon, McClelland, Maier & Neustadt, L.L.P.

(57) ABSTRACT

The present invention relates to the compound of formula (I) wherein $R^{1A}$, $R^{1B}$, $R^{1C}$, and $R^{1D}$ are hydrogen atom, etc., $R^{2A}$ and $R^{2B}$ are hydrogen atom, etc., $R^{3A}$, $R^{3B}$, $R^{3C}$, and $R^{3D}$ are hydrogen atom, etc., L is bond, etc., V is $C_{1-6}$ alkylene, Q is optionally-substituted imidazole, or a pharmaceutically acceptable salt thereof, as a novel anti-tumor agent that targets CSCs which are thought to be closely involved in the persistent proliferation of malignant tumor, metastasis or recurrence of cancer, and resistance to anti-tumor agents.

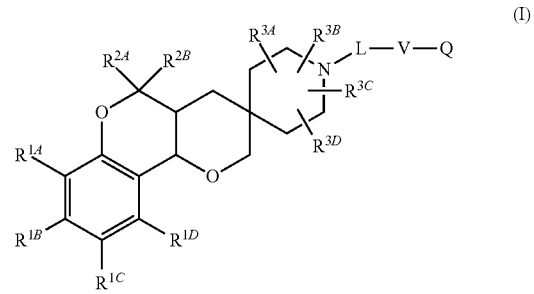

9 Claims, No Drawings

(56) References Cited

OTHER PUBLICATIONS

Bruce M. Boman et al. "Cancer Stem Cells: A Step Toward the Cure" Journal of Clinical Oncology, vol. 26, No. 17, Jun. 10. 2008, pp. 2796-2799.
Neethan A. Lobo, et al. "The Biology of Cancer Stem Cells" Anna. Rev. Cell Dev. Biol. 2007, 23:675-99.
Muhammad Al-Hajj, et al. "Self-Renewal and Solid Tumor Stem Cells" 2004 Nature Publishing Group, Oncogene (2004) 23, pp. 7274-7282.
Dario Ponti, et al. "Isolation and in Vitro Propagation of Tumorigenic Breast Cancer Cells with Stem/Progenitor Cell Properties" Cancer Res 2005; 65: (13), Jul. 1, 2005, pp. 5506-5511.
International Preliminary Report on Patentability and Written Opinion issued Sep. 22, 2020 in PCT/JP2019/011439 (submitting English translation only), 7 pages.
Extended European Search Report issued Nov. 3, 2021 in corresponding European Patent Application No. 19770755.7 citing documents AO, AP and AX therein, 6 pages.
Panarat Arunrattiyakorn et al., "Biotransformation of γ-Mangostin by an Endophytic Fungus of *Garcinia mangostana* to Furnish Xanthenes with an Unprecedented Heterocyclic Skeleton", Journal Of Natural Products, vol. 81, No. 10, Oct. 26, 2018. pp. 2244-2250.
Ahmad et al., Journal of Molecular Liquids, vol. 262, pp. 460-475 (Year: 2018).

\* cited by examiner

DIHYDROCHROMENE DERIVATIVES

This application is a continuation of U.S. Ser. No. 16/944,482, filed Jul. 31, 2020, which is a continuation of Ser. No. 16/808,246 filed Mar. 3, 2020, now U.S. Pat. No. 10,807,993 which is a continuation of PCT/JP2019/011439, filed Mar. 19, 2019, which claims priority to Japanese application 2018-052971 filed Mar. 20, 2018. Priority is claimed to all these applications and the contents of each is incorporated herein by reference in their entirety.

TECHNICAL FIELD

The present invention relates to a dihydrochromene derivative and a pharmaceutically acceptable salt thereof which is useful as a medicament, and relates to an anti-tumor agent comprising the derivative as an active ingredient.

BACKGROUND ART

Conventional cancer treatments are sometimes not expected to bring in meaningful survival effects even if they can induce the regression of tumors, partly because nowadays, it has been suggested that cancer stem cells (hereinafter referred to as "CSCs" as necessary) are closely involved in the persistent proliferation of malignant tumors, metastasis or recurrence of cancer, and resistance to anti-tumor agents. CSCs have been identified in almost all types of major cancers in human such as breast cancer, colon cancer, lung cancer, and hematological malignancy (Non-Patent Literature 1). Also, CSCs can be greatly different in the biological features from normal cancer cells obtained from the differentiation of CSCs, and thus the development of an anti-tumor agent that targets CSCs is expected to lead to a new strategy for cancer treatments (Non-Patent Literature 2).

One of the features in CSCs is the self-renewal ability (Non-Patent Literature 3). Reliable methods established for measuring the self-renewal ability of cells include, for example, a method for measuring the sphere-forming ability of cancer cells in non-adherent condition in the absence of serum (Non Patent Literature 4).

There has been no literature disclosing that the present compounds of formula (1) shown below can exhibit anti-cancer action or inhibitory action of the sphere-forming ability of cancer cells until now.

PRIOR ART

Non-Patent Reference

[Non-Patent Literature 1] Boman et al., Journal of Clinical Oncology 26(17): 2795-2799. 2008
[Non-Patent Literature 2] Lobo et al., Annu Rev Cell Dev Biol 23: 675-99. 2007
[Non-Patent Literature 3] Al-Hajj et al., Oncogene 23(43): 7274-82. 2004
[Non-Patent Literature 4] Ponti et al., Cancer Res 65(13): 5506-11. 2005

SUMMARY OF INVENTION

Technical Problem

An object of the present invention is to provide useful compounds as a novel anti-tumor agent that targets CSCs which are thought to be closely involved in the persistent proliferation of malignant tumor, metastasis or recurrence of cancer, and resistance to anti-tumor agents.

Solution to Problem

The present inventors nave extensively studied to reach the above object, and then have found that a compound of the following Formula (1) or a pharmaceutically acceptable salt thereof (hereinafter referred to as "the present compound", as necessary) has a potent inhibitory effect on the sphere-forming ability of cancer cells and is highly useful as a novel anti-tumor agent. Based upon the findings, the present invention has been achieved.

The present invention is as described below.

(Item 1) A compound of formula (I):

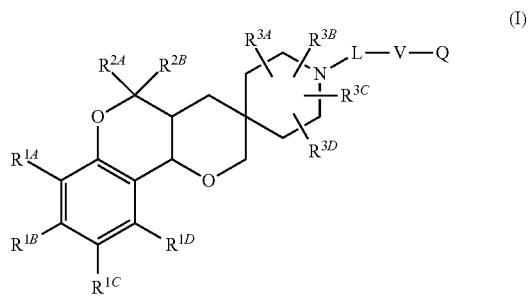

or a pharmaceutically acceptable salt thereof, wherein $R^{1A}$, $R^{1B}$, $R^{1C}$, and $R^{1D}$ are each independently hydrogen atom, halogen atom, azide, or cyano, provided that all of $R^{1A}$, $R^{1B}$, $R^{1C}$, and $R^{1D}$ are not hydrogen atom, $R^{2A}$ and $R^{2B}$ are each independently hydrogen atom or $C_{1-6}$ alkyl, $R^{3A}$, $R^{3B}$, $R^{3C}$, and $R^{3D}$ are each independently hydrogen atom, halogen atom, hydroxy, $C_{1-6}$ alkyl, $C_{1-6}$ alkoxy, —$CO_2R^4$, —$NR^5R^6$, or —$NR^7COR^8$, or any two of $R^{3A}$, $R^{3B}$, $R^{3C}$, and $R^{3D}$ may be taken together at the common carbon atom to which they are attached to form =O, L, is bond or —C(C)—, V is $C_{1-6}$ alkylene which may be substituted with 1 to 3 substituents selected independently from the group consisting of fluorine atom, hydroxy, $C_{1-6}$ alkoxy, $C_{3-7}$ cycloalkyl, 3- to 7-membered saturated heterocyclyl, cyano, and azide, Q is optionally-substituted imidazole group, $R^4$ and $R^8$ are each independently $C_{1-3}$ alkyl, and $R^5$, $R^6$, and $R^7$ are each independently hydrogen atom or $C_{1-3}$ alkyl, or when $R^5$ and $R^6$ are both $C_{1-3}$ alkyl, they may be combined with the nitrogen atom to which they are attached to form 3- to 6-membered nitrogen-containing saturated heterocyclyl, provided that the following compounds of formulae (Z-1) and (Z-2):

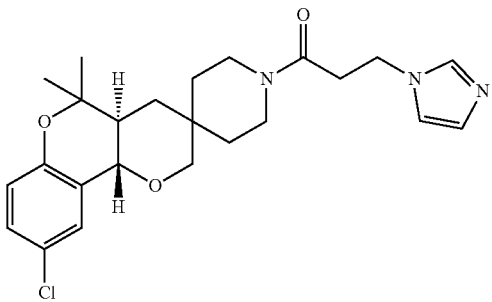

(Z-1)

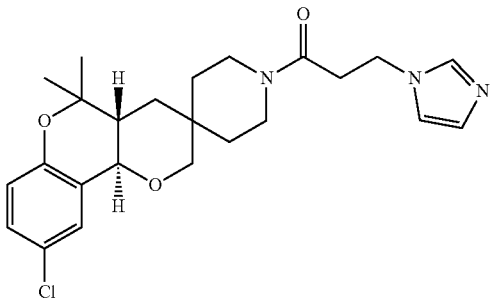

(Z-2)

are excluded.

(Item 2) The compound of Item 1 or a pharmaceutically acceptable salt thereof, wherein
Q is imidazole group which may be substituted with 1 to 3 substituents selected independently from the group consisting of halogen atom, cyano, $C_{1-6}$ alkyl (which may be substituted with 1 to 3 substituents selected independently from the group consisting of halogen atom, cyano, hydroxy, $C_{1-6}$ alkoxy, $-NR^{5a}R^{6a}$, and $-NR^{7a}COR^{8a}$), $C_{2-6}$ alkenyl (which may be substituted with 1 to 3 hydroxy groups), $-CO_2R^{4a}$, and $-CONR^9R^{10}$,
$R^{5a}$, $R^{6a}$, $R^{7a}$, $R^9$, and $R^{10}$ are each independently hydrogen atom or $C_{1-3}$ alkyl, or
when $R^{5a}$ and $R^{6a}$ are both $C_{1-3}$ alkyl, they may be combined with the nitrogen atom to which they are attached to form 3- to 6-membered nitrogen-containing saturated heterocyclyl, and
when $R^9$ and $R^{10}$ are both $C_{1-3}$ alkyl, they may be combined with the nitrogen atom to which they are attached to form 3- to 6-membered nitrogen-containing saturated heterocyclyl, and
$R^{4a}$ and $R^{8a}$ are independently $C_{1-3}$ alkyl.

(Item 3) The compound of Item 1 or 2, or a pharmaceutically acceptable salt thereof, wherein $R^{3A}$, $R^{3B}$, $R^{3C}$, and $R^{3D}$ are hydrogen atom.

(Item 4) The compound of any one of Item 1 to 3, or a pharmaceutically acceptable salt thereof, wherein $R^{2A}$ and $R^{2B}$ are each independently hydrogen atom or $C_{1-3}$ alkyl.

(Item 5) The compound of any one of Items 1 to 3, or a pharmaceutically acceptable salt thereof, wherein $R^{2A}$ and $R^{2B}$ are each independently $C_{1-3}$ alkyl.

(item 6) The compound of any one of Items 1 to 3, or a pharmaceutically acceptable salt thereof, wherein $R^{2A}$ and $R^{2B}$ are methyl.

(Item 7) The compound of any one of Items 1 to 6, or a pharmaceutically acceptable salt thereof, wherein L is bond.

(Item 8) The compound of any one of Items 1 to 6, or a pharmaceutically acceptable salt thereof, wherein L is —CO—.

(Item 9) The compound of any one of Items 1 to 8, or a pharmaceutically acceptable salt thereof, wherein V is $C_{1-6}$ alkylene.

(Item 10) The compound of any one of Items 1 to 8, or a pharmaceutically acceptable salt thereof, wherein: V is $C_{1-3}$ alkylene.

(Item 11) The compound of any one of Items 1 to 8, or a pharmaceutically acceptable salt thereof, wherein V is ethylene.

(Item 12) The compound of any one of Items 1 to 8, or a pharmaceutically acceptable salt thereof, wherein V is methylene.

(Item 13) The compound of any one of Items 1 to 12, or a pharmaceutically acceptable salt thereof, wherein $R^{1A}$, $R^{1B}$, $R^{1C}$, and $R^{1D}$ are each independently hydrogen atom, fluorine atom, or chlorine atom, provided that all of $R^{1A}$, $R^{1B}$, $R^{1C}$, and $R^{1D}$ are not hydrogen atom.

(Item 14) The compound of any one of Items 1 to 13, or a pharmaceutically acceptable salt thereof, wherein Q is formula (Q-1) or (Q-2):

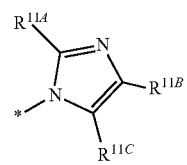

(Q-1)

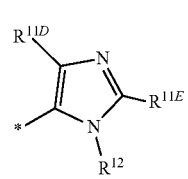

(Q-2)

wherein
$R^{11A}$, $R^{11B}$, $R^{11C}$, $R^{11D}$, and $R^{11E}$ are each independently hydrogen atom, halogen atom, cyano, $C_{1-6}$ alkyl (which may be substituted with 1 to 3 substituents selected independently from the group consisting of halogen atom, cyano, hydroxy, $C_{1-6}$ alkoxy, $-NR^{5a}R^{6a}$, and $-NR^{7a}COR^{8a}$), $C_{2-6}$ alkenyl (which may be substituted with 1 to 3 hydroxy groups), $-CO_2R^{4a}$, or $-CONR^9R^{10}$,
$R^{5a}$, $R^{6a}$, $R^{7a}$, $R^9$, and $R^{10}$ are each independently hydrogen atom or $C_{1-3}$ alkyl, or
when $R^{5a}$ and $R^{6a}$ are both $C_{1-3}$ alkyl, they may be combined with the nitrogen atom to which they are attached to form 3- to 6-membered nitrogen-containing saturated heterocyclyl, and
when $R^9$ and $R^{10}$ are both $C_{1-3}$ alkyl, they may be combined with the nitrogen atom to which they are attached to form 3- to 6-membered nitrogen-containing saturated heterocyclyl,
$R^{4a}$ and $R^{8a}$ are independently $C_{1-3}$ alkyl,
$R^{12}$ is hydrogen atom or $C_{1-6}$ alkyl, and
asterisk (*) is the binding point to V.

(Item 15) The compound of Item 14, or a pharmaceutically acceptable salt thereof, wherein $R^{11A}$, $R^{11B}$, $R^{11C}$, $R^{11D}$, and $R^{11E}$ are each independently hydrogen atom, cyano, $C_{1-6}$ alkyl (which may be substituted with 1 to 3 substituents selected independently from the group consisting of fluorine atom, hydroxy, and $-NR^{7a}COR^{8a}$), $C_{2-6}$ alkenyl. (which may be substituted with one hydroxy group), or $-CO_2R^{4a}$.

(Item 16) The compound of Item 14, or a pharmaceutically acceptable salt thereof, wherein $R^{11A}$, $R^{11B}$, $R^{11C}$, $R^{11D}$, and $R^{11E}$ are each independently hydrogen atom, cyano, $C_{1-3}$ alkyl, or $C_{2-6}$ alkenyl, wherein the alkyl and the alkenyl may be each independently substituted with one hydroxy group.

(Item 17) The compound of Item 14, or a pharmaceutically acceptable salt thereof, wherein $R^{11A}$, $R^{11B}$, $R^{11C}$, $R^{11D}$, and $R^{11E}$ are each independently hydrogen atom or $C_{1-3}$ alkyl.

(Item 18) The compound of any one of Items 14 to 17, or a pharmaceutically acceptable salt thereof, wherein $R^{12}$ is hydrogen atom.

(Item 19) The compound of any one of Items 1 to 18, or a pharmaceutically acceptable salt thereof, wherein formula (I) is formula (1-A):

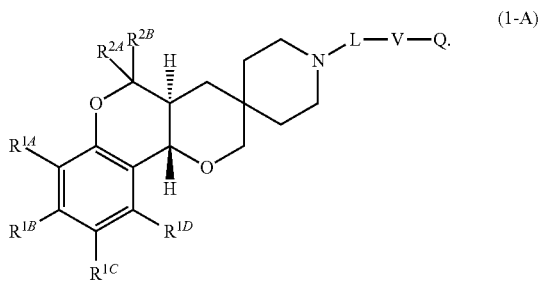

(1-A)

(Item 20) The compound of any one of Items 1 to 18, or a pharmaceutically acceptable salt thereof, wherein formula (I) is formula (1-B):

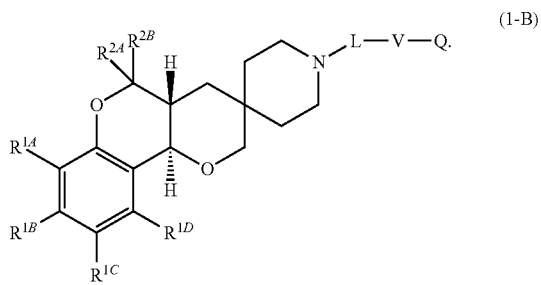

(1-B)

(Item 21) The compound of any one of Items 1 to 18, or a pharmaceutically acceptable salt thereof, wherein formula (I) is formula (1-C):

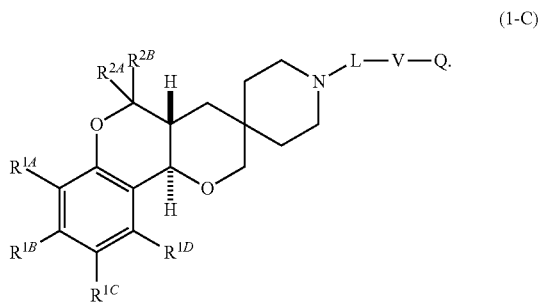

(1-C)

(Item 22) The compound of Item 1 or a pharmaceutically acceptable salt thereof, which is selected from:

(4'aS,10'bS)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran] (Example 18), (4'aR,10'bR)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran] (Example 18), (4'aR,10'bR)-9'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran] (Example 24), (4'aS,10'bS)-9'-chloro-5',5'-dimethyl-1-[4-methyl-1H-imidazol-5-yl)methyl]-4'a,10'b-dihydro-2',4'H,5'H-spiro[piperidine-4,3'-pyrano[3,2-c][1]benzopyran] (Example 24), (4'aS,10'bS)-9'-chloro-5',5'-dimethyl-1-[(1-methyl-1H-imidazol-5-yl)methyl]-4'a,10'b-dihydro-2'H,4'H,5'H-spiro[piperidine-4,3'-pyrano[3,2-c][1]benzopyran] (Example 32), (4'aR,10'bR)-9'-chloro-5',5'-dimethyl-1-[(1-methyl-1H-imidazol-5-yl)methyl]-4'a,10'b-dihydro-2'H,4'H,5'H-spiro[piperidine-4,3'-pyrano[3,2-c][1]benzopyran] (Example 32), (4'aR,10'bR)-8'-chloro-5',5'-dimethyl-1-[(1-methyl-1H-imidazol-5-yl)methyl]-4'a,10'b-dihydro-2'H,4'H,5'H-spiro[piperidine-4,3'-pyrano[3,2-c][1]benzopyran] (Example 33), (4'aS,10'bS)-8'-chloro-5',5'-dimethyl-1-[(1-methyl-1H-imidazol-5-yl)methyl]-4'a,10'b-dihydro-2'H,4'H,5'H-spiro[piperidine-4,3'-pyrano[3,2-c][1]benzopyran] (Example 33), (4'aS,10'bS)-7'-chloro-5',5'-dimethyl-1-[(1-methyl-1H-imidazol-5-yl)methyl]-4'a,10'b-dihydro-2'H,4'H,5'H-spiro[piperidine-4,3'-pyrano[3,2-c][1]benzopyran] (Example 34), (4'aR,10'bR)-7'-chloro-5',5'-dimethyl-1-[(1-methyl-1H-imidazol-5-yl)methyl]-4'a,10'b-dihydro-2'H,4'H,5'H-spiro[piperidine-4,3'-pyrano[3,2-c][1]benzopyran] (Example 34), (4'aR,10'bR)-8'-chloro-1-[2-(1H-imidazol-1-yl)ethyl]-5',5'-dimethyl-4'a,10'b-dihydro-2'H,4'H,5'H-spiro[piperidine-4,3'-pyrano([3,2-c][1]benzopyran) (Example 38), (4'aS,10'bS)-8'-chloro-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran] (Example 38), (4'aS,10'bS)-9'-fluoro-1-[2-(1H-imidazol-1-yl)ethyl]-5'5'-dimethyl-4'a,10'b-dihydro-2'H,4'H,5'H-spiro[piperidine-4,3'-pyrano[3,2-c][1]benzopyran] (Example 39), (4'aR,10'bR)-9'-fluoro-1-[2-(1H-imidazol-1-yl)ethyl]-5'5'-dimethyl-4'a,10'b-dihydro-2'H,4'H,5'4-spiro[piperidine-4,3'-pyrano[3,2-c][1]benzopyran] (Example 39), (4'aR,10'bR)-9'-chloro-1-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran] (Example 40), (4'aS,10'bS)-9'-chloro-1-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran] (Example 40), (4'aS,10'bS)-9'-fluoro-5',5'-dimethyl-1-[2-(2-methyl-1H-imidazol-1-yl)ethyl]-4'a,10'b-d-hydro-2'H,4'H,5'H-spiro[piperidine-4,3'-pyrano[3,2-c][1]benzopyran] (Example 43), (4'aR,10'bR)-9'-fluoro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 43), (4'aR,10'bR)-9'-chloro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 46), (4'aS,10'bS)-9'-chloro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 46), (4'aS,10'bS)-8'-chloro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 49), (4'aR,10'bR)-8'-chloro-5',5'-dimethyl-1-[2-(2-methyl-1H-imidazol-1-yl)ethyl]4'a,10'b-dihydro-2'H,4'H,5'H-spiro[piperidine-4,3'-pyrano[3,2-c][1]benzopyran] (Example 49), (1-{2-[(4'aR,10'bR)-9'-fluoro-5',5'-dimethyl-4'a,10'b-dihydro-2'H,4'H,5'H-spiro[piperidine-4,3'-pyrano[3,2-c][1]benzopyran]-1-yl]ethyl}-1H-imidazol-2-yl) methanol (Example 52), (1-{2-[(4'aS,10'bS)-9'-fluoro-5',5'-dimethyl-4'a,10'b-dihydro-2'H,4'H,5'H-spiro[piperidine-4,3'-pyrano[3,2-c][1]benzopyran]-1-yl]ethyl}-1H-imidazol-2-yl)methanol (Example 52), (1-{2-[(4'aS,10'bS)-9'-chloro-5',5'-dimethyl-4'a,10'b-dihydro-2'H,4'H,5'H-spiro[piperidine-4,3'-pyrano[3,2-c][1]benzopyran]-1-yl]ethyl}-1H-imidazol-2-yl)methanol (Example 53), (1-{2-[(4'aR,10'bR)-9'-chloro-5',5'-dimethyl-4'a,10'b-dihydro-2'H,4'H,5'H-spiro[piperidine-4,3'-pyrano[3,2-c][1]benzopyran]-1-yl]ethyl}-1H-imidazol-2-yl)methanol (Example 53), (1-{2-[(4'aR,10'bR)-8'-chloro-5',5'-dimethyl-4'a,10'b-dihydro-2'H,4'H,5'H-spiro[piperidine-4,3'-pyrano[3,2-c][1]benzopyran]-1-yl]ethyl}-1H-imidazol-2-yl)methanol (Example 54), (1-{2-[(4'aS,10'bS)-8'-chloro-5',5'-dimethyl-4'a,10'b-dihydro-2'H,4'H,5'H-spiro[piperidine-4,3'-pyrano[3,2-c][1]benzopyran]-1-yl]ethyl}-1H-imidazol-2-yl)methanol (Example 54), (1-{2-[(4'aS,10'bS)-9'-chloro-5',5'-dimethyl-4'a,10'b-dihydro-2'H,4'H,5'H-spiro[piperidine-4,3'-pyrano[3,2-c][1]benzopyran]-1-yl]ethyl}-5-methyl-1H-imidazol-4-yl)methanol (Example 56), (1-{2-[(4'aR,10'bR)-9'-chloro-5',5'-dimethyl-4'a,10'b-dihydro-2'H,4'H,5'H-spiro[piperidine-4,3'-pyrano[3,2-c][1]benzopyran]-1-yl]ethyl}-5-methyl-1H-imidazol-4-yl)methanol (Example 56), (4'aS,10'bR)-8'-chloro-1-[(4-methyl-1H-imidazol-5-yl)methyl]-4'a,10'b-dihydro-2'H,4'H,5'H-spiro[piperidine-4,3'-pyrano[3,2-c][1]benzopyran] (Example 64), and (4'aR,10'bS)-8'-chloro-1-[(4-methyl-1H-imidazol-5-yl)methyl]-4'a,10'b-dihydro-2'H,4'H,5'H-spiro[piperidine-4,3'-pyrano[3,2-c][1]benzopyran] (Example 64).

(Item 23) The compound of Item 1 or a pharmaceutically acceptable salt thereof, which is selected from:

(4'aS,10'bS)-8'-chloro-5',5'-dimethyl-1-1(4-methyl-1H-imidazol-5-yl)methyl-4'a,10'b-dihydro-2'H,4'H,5'H-spiro[piperidine-4,3'-pyrano[3,2-c][1]benzopyran] (Example 18), (4'aR,10'bR)-8'-chloro-5',5'-dimethyl-1-[((4-methyl-1H-imidazol-5-yl)methyl]-4'a,10'b-dihydro-2'H,4'H,5'H-spiro[piperidine-4,3'-pyrano[3,2-c][1]benzopyran] (Example 18), (4'aR,10'bR)-9'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran] (Example 24), (4'aS,10'bS)-9'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran] (Example 24), (4'aS,10'bS)-9'-chloro-5',5'-dimethyl-1-[(1-methyl-1H-imidazol-5-yl)methyl]-4'a,10'b-dihydro-2'H,4'H,5'H-spiro[piperidine-4,3'-pyrano[3,2-c][1]benzopyran] (Example 32), (4'aR,10'bR)-9'-chloro-5',5'-dimethyl-1-[(1-methyl-1H-imidazol-5-yl)methyl]-4'a,10'b-dihydro-2'H,4'H,5'H-spiro[piperidine-4,3'-pyrano[3,2-c][1]benzopyran] (Example 32), (4'aR,10'bR)-8'-chloro-5',5'-dimethyl-1-[(1-methyl-1H-imidazol-5-yl)methyl]-4'a,10'b-dihydro-2'H,4'H,5'H-spiro[piperidine-4,3'-pyrano[3,2-c][1]benzopyran] (Example 33), 4'aS,10'bS)-8'-chloro-5',5'-dimethyl-1-[(1-methyl-1H-imidazol-5-yl)methyl]-4'a,10'b-dihydro-2'H,4'H,5'H-spiro[piperidine-4,3'-pyrano[3,2-c][1]benzopyran] (Example 33), (4'aS,10'bS)-7'-chloro-5',5'-dimethyl-1-[((1-methyl-1H-imidazol-5-yl)methyl]-4'a,10'b-dihydro-2'H,4'H,5'H-spiro[piperidine-4,3'-pyrano[3,2-c][1]benzopyran] (Example 34), and (4'aR,10'bR)-7'-chloro-5',5'-dimethyl-1-[(1-methyl-1H-imidazol-5-yl)methyl]-4'a,10'b-dihydro-2'H,4'H,5'H-spiro[piperidine-4,3'-pyrano[3,2-c][1]benzopyran] (Example 34).

(Item 24) The compound of Item 1 or a pharmaceutically acceptable salt thereof, which is selected from:

(4'aR,10'bR)-8'-chloro-1-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran] (Example 38), (4'aS,10'bS)-8'-chloro-1-[2-(1H-imidazol-1-yl)ethyl]-5',5'-dimethyl-4'a,10'b-dihydro-2',4'H,5'H-spiro[piperidine-4,3'-pyrano[3,2-c][1]benzopyran] (Example 38), (4'aS,10'bS)-9'-fluoro-1-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran] (Example 39), (4'aR,10'bR)-9'-fluoro-1-[2-(1H-imidazol-1-yl)ethyl]-5',5'-dimethyl-4'a,10'b-dihydro-2'H,4'a,5'H-spiro[piperidine-4,3'-pyrano[3,2-c][1]benzopyran] (Example 39), (4'aR,10'bR)-9'-chloro-1-[2-(1H-imidazol-1-yl)ethyl]-5,5'-dimethyl-4'a,10'b-dihydro-2'H,4',5'H-spiro[piperidine-4,3'-pyrano[3,2-c][1]benzopyran] (Example 40), (4'aS,10'bS)-9'-chloro-1-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran] (Example 40), (4'aS,10'bS)-9'-fluoro-5',5'-dimethyl-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 43), (4'aR,10'bR)-9'-fluoro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 43), (4'aR,10'bR)-9'-chloro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 46), (4'aS,10'bS)-9'-chloro-5',5'-dimethyl-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 46), (4'aS,10'bS)-8'-chloro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 49), (4'aR,10'bR)-8'-chloro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 49), (1-{2-[(4'aR,10'bR)-9'-fluoro-5',5'-dimethyl-4'a,10'b-dihydro-2'H,4'H,5'H-spiro[piperidine-4,3'-pyrano[3,2-c][1]benzopyran]-1-yl]ethyl}-1H-imidazol-2-yl)methanol (Example 52), (1-{2-[(4'aS,10'bS)-9'-fluoro-5',5'-dimethyl-4'a,10'b-dihydro-2'H,4'H,5'H-spiro[piperidine-4,3'-pyrano[3,2-c][1]benzopyran]-1-yl]ethyl}-1H-imidazol-2-yl) methanol (Example 52), (1-{2-[(4'aS,10'bS)-9'-chloro-5',5'-dimethyl-4'a,10'b-dihydro-2'H,4'H,5'H-spiro[piperidine-4,3'-pyrano([3,2-c][1]benzopyran]-1-yl]ethyl}-1H-imidazol-2-yl)methanol (Example 53), (1-{2-[(4'aR,10'bR)-9'-chloro-5',5'-dimethyl-4'a,10'b-dihydro-2'H,4'H,5'H-spiro[piperidine-4,3'-pyrano[3,2-c][1]benzopyran]-1-yl]ethyl}-1H-imidazol-2-yl)methanol (Example 53), (1-{2-[(4'aR,10'bR)-8'-chloro-5',5'-dimethyl-4'a,10'b-dihydro-2'H,4'H,5'H-spiro[piperidine-4,3'-pyrano[3,2-c][1]benzopyran]-1-yl]ethyl}-1H-imidazol-2-yl)methanol (Example 54), (1-{2-[(4'aS,10'bS)-8'-chloro-5',5'-dimethyl-4'a,10'b-dihydro-2'H,4'H,5'H-spiro[piperidine-4,3'-pyrano[3,2-c][1]benzopyran]-1-yl]ethyl}-1H-imidazol-2-yl)methanol (Example 54), (1-{2-[(4'aS,10'bS)-9'-chloro-5',5'-dimethyl-4'a,10'b-dihydro-2'H,4'H,5'H-spiro[piperidine-4,3'-pyrano[3,2-c][1]benzopyran]-1-yl]ethyl}-5-methyl-1H-imidazol-4-yl)methanol (Example 56), and (1-{2-[(4'aR,10'bR)-9'-chloro-5',5'-dimethyl-4'a,10'b-dihydro-2'H,4'H,5'H-spiro[piperidine-4,3'-pyrano[3,2-c][1]benzopyran]-1-yl]ethyl}-5-methyl-1H-imidazol-4-yl)methanol (Example 56).

(Item 25) The compound of item 1 or a pharmaceutically acceptable salt thereof, which is selected from:

(4'aS,10'bS)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran] (Example 18), (4'aR,10'bR)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran] (Example 18), (4'aR,10'bR)-8'-chloro-1-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran] (Example 38), (4'aS,10'bS)-8'-chloro-1-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran] (Example 38), (4'aS,10'bS)-9'-fluoro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 43), and (4'aR,10'bR)-9'-fluoro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 43).

(Item 26) The compound of Item 1 or a pharmaceutically acceptable salt thereof, which is selected from:

(4'aS,10'bS)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran] (Example 18).

(Item 27) The compound of Item 1 or a pharmaceutically acceptable salt thereof, which is selected from:

(4'aR,10'bR)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran] (Example 18).

(Item 26) The compound of Item 1 or a pharmaceutically acceptable salt thereof, which is selected from:

(4'aR,10'bR)-8'-chloro-1-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran] (Example 38).

(Item 29) The compound of Item 1 or a pharmaceutically acceptable salt thereof, which is selected from:

(4'aS,10'bS)-8'-chloro-1-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran] (Example 38).

(Item 30) The compound of Item 1 or a pharmaceutically acceptable salt thereof, which is selected from:

(4'aS,10'bS)-9'-fluoro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 43).

(Item 31) The compound of Item 1, or a pharmaceutically acceptable salt thereof, which is selected from:

(4'aR,10'bR)-9'-fluoro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 43).

(Item 32) The compound of item 1 or a phosphate thereof, which is selected from:

(4'aS,10'bS)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran] (Example 18), (4'aR,10'bR)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran] (Example 18), (4'aR,10'bR)-8'-chloro-1-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran] (Example 38), (4'aS,10'bS)-8'-chloro-1-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran] (Example 38), (4'aS,10'bS)-9'-fluoro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 43), and (4'aR,10'bR)-9'-fluoro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 43).

(Item 33) The compound of item 1 or a fumarate thereof, which is selected from:

(4'aS,10'bS)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran] (Example 18), 4'aR,10'bR)-8'-chloro-5',5'-dimethyl-1-[(4-1H-imidazol-5-yl)methyl]-4'a,10'b-dihydro-2'H,4'H,5'H-spiro[piperidine-4,3'-pyrano[3,2-c][1]benzopyran] (Example 18), (4'aR,10'bR)-8'-chloro-1-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran] (Example 38), (4'aS,10'bS)-8'-chloro-1-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran] (Example 38), (4'aS,10'bS)-9'-fluoro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 43), and (4'aR,10'bR)-9'-fluoro-5',5'-dimenthyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 43).

(Item 34) The compound of Item 1 or a p-toluenesulfonate thereof, which is selected from:

(4'aS,10'bS)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran] (Example 18), (4'aR,10'bR)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran] (Example 18), (4'aR,10'bR)-8'-chloro-1-[2-(1H-imidazol-1-yl)ethyl]-5',5'-diethyl-4'a,10'b-dihydro-2'H,4'H,5'-spiro[piperidine-4,3'-pyrano[3,2-c][1]benzopyran] (Example 38), (4'aS,10'bS)-8'-chloro-1-[2-(1H-imidazo-1-yl)ethyl]-5',5'-dimethyl-4'a,10'b-dihydro-2'H,4'H,5'H-spiro[piperidine-4,3'-pyrano[3,2-c][1]benzopyran] (Example 38), (4'aS,10'bS)-9'-fluoro-5',5'-dimethyl-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 43), and (4'aR,10'bR)-9'-fluoro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran] (Example 43).

(Item 35) A medicament comprising the compound of any one of Items 1 to 34 or a pharmaceutically acceptable salt thereof as an active ingredient.

(Item 36) An antitumor medicament comprising the compound of any one of items 1 to 34 or a pharmaceutically acceptable salt thereof as an active ingredient.

(Item 37) The antitumor medicament of Item 36, wherein the tumor is acute leukemia, chronic lymphocytic leukemia, chronic myeloid leukemia, polycythemia vera, malignant lymphoma, myeloma, brain tumor, head and neck cancer, esophageal cancer, thyroid cancer, small cell lung cancer, non-small-cell lung cancer, breast cancer, gastric cancer, gallbladder/bile duct cancer, liver cancer, pancreatic cancer, colon cancer, rectal cancer, ovarian cancer, chorionepithelioma, uterine body cancer, cervical cancer, urothelial carcinoma, renal cell cancer, prostate cancer, testicular neoplasm, Wilms' tumor, malignant melanoma, neuroblastoma, osteosarcoma, Ewing's sarcoma, or soft tissue sarcoma.

(Item 38) A pharmaceutical composition comprising the compound of any one of Items 1 to 34 or a pharmaceutically acceptable salt thereof, which is used in combination with another agent or a pharmaceutically acceptable salt thereof, wherein the another agent is at least one agent selected from the group consisting of an anticancer alkylating agent, an anticancer antimetabolite, an anticancer antibiotic, a plant-derived anticancer medicament, an anticancer platinum complex compound, an anticancer camptothecin derivative, an anticancer tyrosine kinase inhibitor, an anticancer serine/threonine kinase inhibitor, an anticancer phospholipid kinase inhibitor, an anticancer monoclonal antibody, interferon, a biological response modifier, a hormone preparation, an angiogenic inhibitor, an immune checkpoint inhibit or, an epigenetics-associated molecular inhibitor, a protein post-translational modification inhibitor, a proteasome inhibitor, and other antitumor medicaments.

(Item 39) The compound of any one of Items 1 to 34 or a pharmaceutically acceptable salt thereof for treating cancer, which is used in combination with another agent or a pharmaceutically acceptable salt thereof, wherein the another agent is at least one agent selected from the group consisting of an anticancer alkylating agent, an anticancer antimetabolite, an anticancer antibiotic, a plant-derived anticancer medicament, an anticancer platinum complex compound, an anticancer camptothecin derivative, an anticancer tyrosine kinase inhibitor, an anticancer serine/threonine kinase inhibitor, an anticancer phospholipid kinase inhibitor, an anticancer monoclonal antibody, interferon, a biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicaments.

(item 40) A method for treating cancer comprising administrating the compound of any one of Items 1 to 34 or a pharmaceutically acceptable salt thereof to a patient in need thereof.

(Item 41) Use of the compound of any one of Items 1 to 34 or a pharmaceutically acceptable salt thereof in the manufacture of a medicament for treating cancer.

(Item 42) A pharmaceutical composition comprising the compound of any one of items 1 to 34 or a pharmaceutically acceptable salt thereof for use in the treatment of cancer.

Effect of the Invention

The compound of the present invention can exhibit an inhibitory effect on the forming ability of CSC, and thereby it is useful as anti-tumor drug. In an additional preferred embodiment, the compound of the present invention is expected to be highly safe since it has a large deviation between the concentration of inhibiting cell proliferation and the concentration of inhibiting hERG current.

DESCRIPTION OF EMBODIMENTS

Hereinafter, the terms used herein are explained as follows.

In case that "optionally-substituted" or "substituted" is used in the definition of substituent groups, the number of the substituting groups is not limited as long as the substitutions are available, i.e., it is one or more.

Unless otherwise specified, the definition of each substituent group also extends over the case of partially-including the substituent group or the case of the substituent group existing on another substituent group.

The "halogen atom" includes, for example, fluorine atom, chlorine atom, bromine atom, and iodine atom. It is preferably fluorine atom or chlorine atom.

The "$C_{1-6}$ alkyl" means alkyl having 1 to 6 carbon atoms, and the same is applied to the case of the other carbon numbers.

The "$C_{1-6}$ alkyl" means straight or branched, chain saturated hydrocarbon group having 1 to 6 carbon atoms. The $C_{1-6}$ alkyl includes preferably "$C_{1-4}$ alkyl", more preferably "$C_{1-3}$ alkyl". The "$C_{1-3}$ alkyl" includes, for example, methyl, ethyl, propyl, 1-methylethyl, and the like. The "$C_{1-4}$ alkyl" includes, for example, butyl, 1,1-dimethylethyl, 1-methylpropyl, 2-methylpropyl, and the like, besides the examples listed in the said "$C_{1-3}$ alkyl". The "$C_{1-6}$ alkyl" includes, for example, pentyl, 1,1-dimethylpropyl, 1,2-dimethylpropyl, 1-methylbutyl, 2-methylbutyl, 4-methylpentyl, 3-methylpentyl, 2-methylpentyl, 1-methylpentyl, hexyl, and the like, besides the examples listed in the said "$C_{1-4}$ alkyl".

The "$C_{2-6}$ alkenyl" means straight or branched chain unsaturated hydrocarbon group having 2 to 6 carbon atoms and 1 to 3 double bonds. The "$C_{2-6}$ alkenyl" includes preferably "$C_{2-4}$ alkenyl". The "$C_{2-4}$ alkenyl" includes, for example, vinyl, propenyl, methylpropenyl, butenyl, and the like. The "$C_{2-6}$ alkenyl" includes, for example, pentenyl, hexenyl, and the like, besides the examples listed in the said "$C_{2-4}$ alkenyl".

The "$C_{1-6}$ alkoxy" means "$C_{1-6}$ alkyloxy", and the part "$C_{1-6}$ alkyl" is as defined in the said "$C_{1-6}$ alkyl". The "$C_{1-6}$ alkoxy" includes preferably "$C_{1-4}$ alkoxy", more preferably "$C_{1-3}$ alkoxy". The "$C_{1-3}$ alkoxy" includes, for example, methoxy, ethoxy, propoxy, 1-methylethoxy, and the like. The "$C_{1-4}$ alkoxy" includes, for example, butoxy, 1,1-dimethylethoxy, 1-methylpropoxy, 2-methylpropoxy, and the like, besides the examples listed in the said "$C_{1-3}$ alkoxy". The "$C_{1-6}$ alkoxy" includes, for example, pentyloxy, 1,1-dimethylpropoxy, 1,2-dimethylpropoxy, 1-methylbutoxy, 2-methylbutoxy, 4-methylpentyloxy, 3-methylpentyloxy, 2-methylpentyloxy, 1-methylpentyloxy, hexyloxy, and the like, besides the examples listed in the said "$C_{1-4}$ alkoxy".

The "$C_{1-6}$ alkylene" means divalent straight or branched chain saturated hydrocarbon group having 1 to 6 carbon atoms. The "$C_{1-6}$ alkylene" includes preferably "$C_{1-3}$ alkylene". The "$C_{1-3}$ alkylene" includes, for example, methylene, ethylene, propylene, 1-methylethylene, and the like.

The "$C_{3-7}$ cycloalkyl" means cyclic saturated hydrocarbon group having 3 to 7 carbon atoms, which may have a partially-unsaturated bond or a bridged structure. The "$C_{3-7}$ cycloalkyl" includes, for example, cyclopropyl, cyclobutyl, cyclopentyl, cyclohexyl, cycloheptyl, and the like.

The "3- to 7-membered saturated heterocyclyl" means saturated heterocycle consisting of 3 to 7 atoms comprising carbon atoms and 1 to 2 atoms selected independently from the group consisting of nitrogen atom, oxygen atom and sulfur atom, which may have a partially-unsaturated bond and a bridged structure. The "3- to 7-membered saturated heterocyclyl" generally includes "3- to 7-membered monocyclic saturated heterocycyl", preferably, "4- to 7-membered monocyclic saturated heterocyclyl", more preferably "5- or 6-membered monocyclic saturated heterocyclyl". The "5- or 6-membered monocyclic saturated heterocyclyl" includes, for example, tetrahydrofuryl, pyrrolidinyl, imidazolidinyl, piperidinyl, morpholinyl, thiomorpholinyl, dioxothiomorpholinyl, hexamethyleneiminyl, oxazolidinyl, thiazolidinyl, oxoimidazolidinyl, dioxoimidazolidinyl, oxoxazolidinyl, dioxooxazolidinyl, dioxothiazolidinyl, tetrahydrofuranyl, tetrahydropyranyl, and the like. The "3- to 7-membered monocyclic saturated heterocyclyl" includes, for example, epoxy, aziridine, oxetanyl, azetidine, and the like, besides the examples listed in the said "5- or 6-membered monocyclic saturated heterocyclyl".

The "imidazole group" means imidazole ring group, which may be also referred to as imidazolyl group. The imidazole group should not be limited as long as the direct binding position is a carbon atom or a nitrogen atom which is composed of the imidazole ring, which includes the following formulae. In the following formulae, * denotes the binding position. In the following formulae, when the binding position is carbon atom, structures wherein the NH group of the imidazole ring is substituted with methyl group are exemplified.

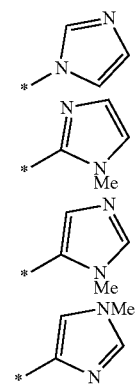

The "cancer" and "tumor" are used interchangeably, and the both mean malignant neoplasm, which encompasses cancer, sarcoma, and hematologic malignancy. The "cancer" and "tumor" include, for example, acute leukemia, chronic lymphocytic leukemia, chronic myeloid leukemia, myelodysplastic syndrome, adult T-cell leukemia/lymphoma, polycythemia vera, malignant lymphoma, myeloma, brain tumor, head and neck cancer, esophageal cancer, thyroid cancer, small cell lung cancer, non-small-cell lung cancer, breast cancer, gastric cancer, gallbladder/bile duct cancer, liver cancer, pancreatic cancer, colon cancer, rectal cancer, ovarian cancer, chorionepithelioma, uterine body cancer, cervical cancer, urothelial carcinoma, renal cell cancer, prostate cancer, testicular neoplasm, Wilms' tumor, malignant melanoma, neuroblastoma, osteosarcoma, Ewing's sarcoma, chondrosarcoma, soft tissue sarcoma, skin cancer, and the like.

The compound shown herein like the following formula

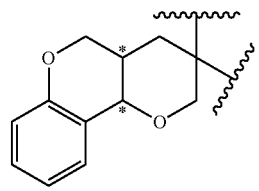

(Y)

may include 4 stereoisomers which are derived from the stereochemistries of the two carbon atoms at the fused parts of the tetrahydropyranochromene ring (two * parts). That is, the compound of formula (Y) encompasses at least one compound selected from 4 stereoisomers having the following formulae (Y-1), (Y-2), (Y-3), and (Y-4):

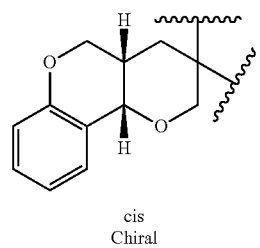

(Y-1)

cis
Chiral (Y-2)

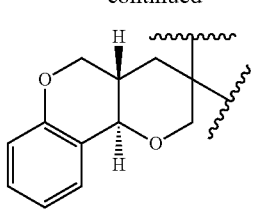

trans
Chiral (Y-3)

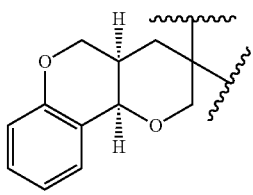

cis
Chiral (Y-4)

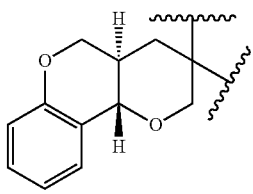

trans
Chiral wherein the stereochemistries of the carbon atoms at the fused parts of formulae (Y-1), (Y-2), (Y-3), and (Y-4) are shown in absolute configuration.

The racemates of the compound of formula (Y) include cis- and trans-forms of the following formulae (Y-5) and (Y-6):

(Y-5)

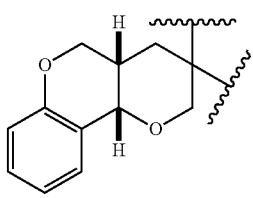

cis
Racemate (Y-6)

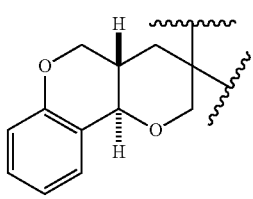

trans
Racemate wherein the stereochemistries of the carbon atoms at the fused parts of formulae (Y-5) and (Y-6) are shown in relative configuration, i.e., one of the two stereoisomers in each a configuration is shown.

The stereochemistry of all compounds shown in the present description should be defined based on the stereochemistry of the specified chemical structures or chemical names. In case that the stereochemistry is not explicitly defined, the stereochemistry may include plural stereoisomers like the above formula (Y).

In the present description, the "binding bar" crossing a ring like the following formula (W) means that substituent "R" attaches at any substitutable site of the ring. For example, the following formula (W):

(W)

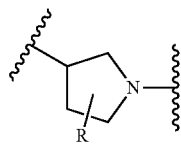

means the following formula (W-1), (W-2), (W-3), or (W-4):

(W-1)

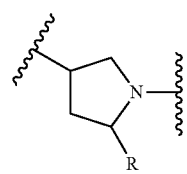

(W-2)

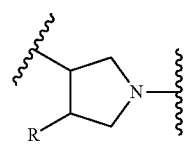

(W-3)

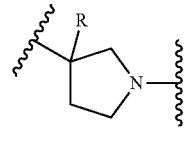

(W-4)

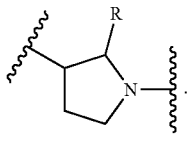

In the present compound of formula (1), preferred $R^{1A}$, $R^{1B}$, $R^{1C}$, $R^{1D}$, $R^{2A}$, $R^{2B}$, $R^{3A}$, $R^{3B}$, $R^{3C}$, $R^{3D}$, $R^4$, $R^{4a}$, $R^5$, $R^{5a}$, $R^6$, $R^{6a}$, $R^7$, $R^{7a}$, $R^8$, $R^{8a}$, $R^9$, $R^{10}$, $R^{11A}$, $R^{11B}$, $R^{11C}$, $R^{11D}$, $R^{11E}$, $R^{12}$, L, V, and Q are as follows, but the technical scope of the present invention is not limited to the scope of compounds listed below.

$R^{1A}$ includes preferably hydrogen atom, fluorine atom, chlorine atom, and bromine atom. It is more preferably hydrogen atom.

$R^{1B}$ includes preferably hydrogen atom, fluorine atom, chlorine atom, and bromine atom. It is more preferably fluorine atom or chlorine atom, even more preferably chlorine atom.

$R^{1C}$ includes preferably hydrogen atom, fluorine atom, chlorine atom, and bromine atom. It is more preferably fluorine atom or chlorine atom, even more preferably chlorine atom.

$R^{1D}$ includes preferably hydrogen atom, fluorine atom, chlorine atom, and bromine atom. It is more preferably hydrogen atom.

In an embodiment of $R^{1A}$, $R^{1B}$, $R^{1C}$, and $R^{1D}$, $R^{1A}$, $R^{1C}$, and $R^{1D}$ are hydrogen atom, and $R^{1B}$ is fluorine atom. In another embodiment, $R^{1A}$, $R^{1C}$, and $R^{1D}$ are hydrogen atom, and $R^{1B}$ is chlorine atom. In a different embodiment of $R^{1A}$, $R^{1B}$, $R^{1C}$, and $R^{1D}$, $R^{1A}$, $R^{1B}$, and $R^{1D}$ are hydrogen atom, and $R^{1C}$ is fluorine atom. In another embodiment, $R^{1A}$, $R^{1B}$, and $R^{1D}$ are hydrogen atom, and $R^{1C}$ is chlorine atom.

$R^{2A}$ includes preferably hydrogen atom and $C_{1-3}$ alkyl. It is more preferably methyl.

$R^{2B}$ includes preferably hydrogen atom and $C_{1-3}$ alkyl. It is more preferably methyl.

In an embodiment, $R^{2A}$ and $R^{2B}$ are both methyl.

$R^{3A}$, $R^{3B}$, $R^{3C}$, and $R^{3D}$ are preferably hydrogen atom.

$R^4$ and $R^{4a}$ include preferably $C_{1-3}$ alkyl. It is more preferably methyl.

$R^5$ and $R^{5a}$ include preferably hydrogen atom and $C_{1-3}$ alkyl.

$R^6$ and $R^{6a}$ include preferably hydrogen atom and $C_{1-3}$ alkyl.

$R^7$ and $R^{7a}$ include preferably hydrogen atom and $C_{1-3}$ alkyl.

$R^8$ and $R^{8a}$ include preferably $C_{1-3}$ alkyl.

$R^9$ includes preferably hydrogen atom and $C_{1-3}$ alkyl.

$R^{10}$ includes preferably hydrogen atom and $C_{1-3}$ alkyl.

$R^{11A}$, $R^{11B}$, and $R^{11C}$ include preferably hydrogen atom, cyano, and $C_{1-3}$ alkyl which may be substituted with one hydroxy. It is more preferably hydrogen atom or methyl, even more preferably hydrogen atom.

$R^{11D}$ includes preferably hydrogen atom and $C_{1-3}$ alkyl. It is more preferably methyl.

$R^{11E}$ includes preferably hydrogen atom, $C_{1-3}$ alkyl, and $C_{2-6}$ alkenyl which may be substituted with one hydroxy. It is more preferably hydrogen atom.

$R^{12}$ includes preferably hydrogen atom and $C_{1-3}$ alkyl. It is more preferably hydrogen atom.

In an embodiment, L is bond. In another embodiment, L is —C(O)—.

V includes preferably $C_{1-3}$ alkylene. It is more preferably methylene or ethylene. In an embodiment, V is methylene. In another embodiment, V is ethylene.

Q includes preferably imidazole group which may be substituted with 1 to 3 substituents selected independently from the group consisting of cyano; $C_{1-3}$ alkyl which may be substituted with 1 to 3 substituents selected independently from the group consisting of hydroxy and —NR$^{7a}$COR$^{8a}$; and $C_{2-6}$ alkenyl which may be substituted with one hydroxy. In an embodiment, Q is formula (Q-1). In another embodiment, Q is formula (Q-2). In an embodiment of $R^{11A}$, $R^{11B}$, and $R^{11C}$ in formula (Q-1), $R^{11A}$, $R^{11B}$, and $R^{11C}$ are all hydrogen atom. In another embodiment, $R^{11A}$ is methyl, and $R^{11B}$ and $R^{11C}$ are both hydrogen atom. In an embodiment of $R^{11D}$, $R^{11E}$, and $R^{12}$ in formula (Q-2), $R^{11D}$ is methyl, and $R^{11E}$ and $R^{12}$ are hydrogen atom.

The compound of formula (1) may include 4 stereoisomers which are derived from the stereochemistries of the two carbon atoms in the fused parts of the tetrahydropyranochromene ring (two * parts).

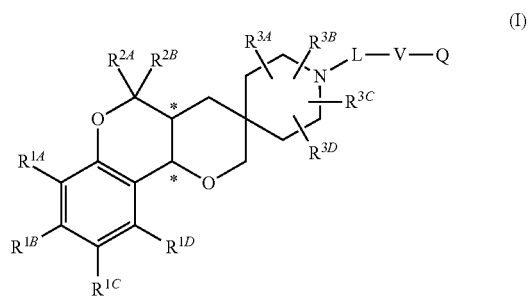

In more detail, the compound of formula (1) encompasses 4 fused-ring compounds having the above-mentioned formulae (Y-1), (Y-2), (Y-3), and (Y-4).

The compounds of formulae (1-A) and (1-B) shown below are trans-fused tetrahydropyranochromene rings, wherein the stereochemistries of the two carbon atoms at the fused parts in formulae (1-A) and (1-B) are shown in absolute configuration.

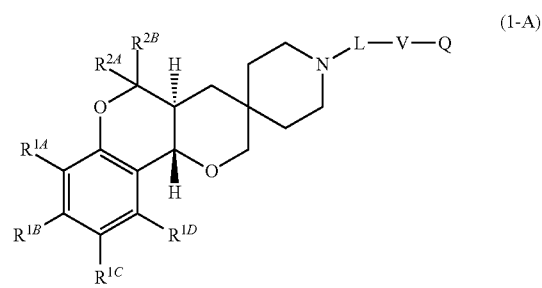

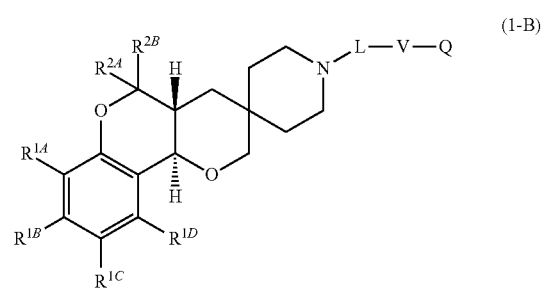

The two compounds of formulae (1-A) and (1-B) are enantiomers each other, i.e., the stereochemistries of the two carbon atoms at the fused parts in the tetrahydropyranochromene ring are the opposite, if there is no chiral carbon other than in the tetrahydropyranochromene ring.

The compound of formula (1-C) is shown in relative configuration wherein the tetrahydropyranochromene ring is a trans-fused ring though the following structure of formula (1-C) shows one stereochemistry having dashed line and thick line from the two carbon atoms for convenience.

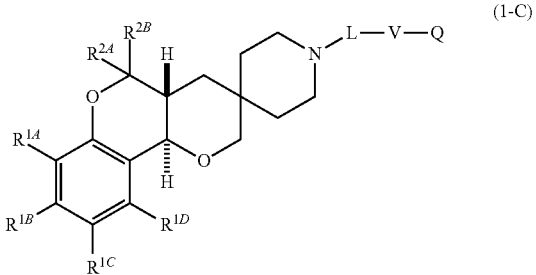
(1-C)

The compound containing the both stereoisomers of formulae (1-A) and (1-B) in equal amount may be shown with formula (1-C).

In an embodiment, the present compound of formula (1) includes the following (A).

(A)

A compound or a pharmaceutically acceptable salt thereof, wherein
$R^{1A}$, $R^{1B}$, $R^{1C}$, and $R^{1D}$ are each independently hydrogen atom, fluorine atom, or chlorine atom, provided that all of $R^{1A}$, $R^{1B}$, $R^{1C}$, and $R^{1D}$ are not hydrogen atom,
$R^{2A}$ and $R^{2B}$ are each independently hydrogen atom or $C_{1-3}$ alkyl,
$R^{3A}$, $R^{3B}$, $R^{3C}$, and $R^{3D}$ are all hydrogen atom,
L is bond or —C(O)—,
V is $C_{1-3}$ alkylene, and
Q is imidazole group which may be substituted with 1 to 3 substituents selected independently from the group consisting of cyano; $C_{1-3}$ alkyl which may be substituted with 1 to 3 substituents selected independently from the group consisting of hydroxy and —$NR^{7a}COR^{8a}$; and $C_{2-6}$ alkenyl which may be substituted with one hydroxy.

In an embodiment, the present compound of formula (1) includes the following (B).

(B)

A compound or a pharmaceutically acceptable salt thereof, wherein
$R^{1A}$, $R^{1B}$, $R^{1C}$, and $R^{1D}$ are each independently hydrogen atom, fluorine atom, or chlorine atom, provided that all of $R^{1A}$, $R^{1B}$, $R^{1C}$, and $R^{1D}$ are not hydrogen atom,
$R^{2A}$ and $R^{2B}$ are each independently hydrogen atom or methyl,
$R^{3A}$, $R^{3B}$, $R^{3C}$, and $R^{3D}$ are all hydrogen atom,
L is bond,
V is $C_{1-3}$ alkylene, and
Q is imidazole group which may be substituted with 1 to 3 substituents selected independently from the group consisting of cyano; $C_{1-3}$ alkyl which may be substituted with 1 to 3 substituents selected independently from the group consisting of hydroxy and —$NR^{7a}COR^{8a}$; and $C_{2-6}$ alkenyl which may be substituted with one hydroxy.

In an embodiment, the present compound of formula (1) includes the following (C).

(C)

A compound or a pharmaceutically acceptable salt thereof, wherein
$R^{1A}$, $R^{1B}$, $R^{1C}$, and $R^{1D}$ are each independently hydrogen atom, fluorine atom, or chlorine atom, provided that all of $R^{1A}$, $R^{1B}$, $R^{1C}$, and $R^{1D}$ are not hydrogen atom,
$R^{2A}$ and $R^{2B}$ are each independently hydrogen atom or methyl,
$R^{3A}$, $R^{3B}$, $R^{3C}$, and $R^{3D}$ are all hydrogen atom,
L is bond,
V is methylene, and
Q is imidazole group which may be substituted with 1 to 2 substituents selected independently from the group consisting of $C_{1-3}$ alkyl and $C_{2-6}$ alkenyl which may be substituted with one hydroxy.

In an embodiment, the present compound of formula (1) includes the following (D).

(D)

A compound or a pharmaceutically acceptable salt thereof, wherein
$R^{1A}$, $R^{1B}$, $R^{1C}$, and $R^{1D}$ are each independently hydrogen atom, fluorine atom, ox chlorine atom, provided that all of $R^{1A}$, $R^{1B}$, $R^{1C}$, and $R^{1D}$ are not hydrogen atom,
$R^{2A}$ and $R^{2B}$ are hydrogen atom or methyl,
$R^{3A}$, $R^{3B}$, $R^{3C}$, and $R^{3D}$ are all hydrogen atom,
L is bond,
V is ethylene, and
Q is imidazole group which may be substituted with 1 to 3 substituents selected independently from the group consisting of cyano and $C_{1-3}$ alkyl which may be substituted with 1 to 2 hydroxy.

In an embodiment, the present compound of formula (1) includes the following (E).

(E)

A compound or a pharmaceutically acceptable salt thereof, wherein
$R^{1A}$, $R^{1B}$, $R^{1C}$, and $R^{1D}$ are each independently hydrogen atom, fluorine atom, or chlorine atom, provided that all of $R^{1A}$, $R^{1B}$, $R^{1C}$, and $R^{1D}$ are not hydrogen atom,
$R^{2A}$ and $R^{2B}$ are hydrogen atom or methyl,
$R^{3A}$, $R^{3B}$, $R^{3C}$, and $R^{3D}$ are all hydrogen atom,
L is bond,
V is ethylene,
Q is formula (Q-1), and
$R^{11A}$, $R^{11B}$, and $R^{11C}$ are each independently hydrogen atom, cyano, $C_{1-3}$ alkyl, or $C_{2-6}$ alkenyl, wherein the alkyl and the alkenyl may be each independently substituted with one hydroxy group.

In an embodiment, the present compound of formula (1) includes the following (F).

(F)

A compound or a pharmaceutically acceptable salt thereof, wherein
$R^{1A}$, $R^{1B}$, $R^{1C}$, and $R^{1D}$ are each independently hydrogen atom, fluorine atom, or chlorine atom, provided that all of $R^{1A}$, $R^{1B}$, $R^{1C}$, and $R^{1D}$ are not hydrogen atom,
$R^{2A}$ and $R^{2B}$ are hydrogen atom or methyl,
$R^{3A}$, $R^{3B}$, $R^{3C}$, and $R^{3D}$ axe all hydrogen atom,
L is bond,
V is methylene,
Q is formula (Q-2),
$R^{11D}$ and $R^{11E}$ are each independently hydrogen atom, cyano, $C_{1-3}$ alkyl, or $C_{2-6}$ alkenyl, wherein the alkyl and the alkenyl may be each independently substituted with one hydroxy group, and
$R^{12}$ is hydrogen atom or $C_{1-6}$ alkyl.

The compound of formula (1) can sometimes exist as a tautomer thereof. Thus, the compound of the present invention also includes a tautomer of compound (1).

The compound of formula (1) can sometimes have at least one chiral carbon atom. Thus, the compound of the present invention also includes an optically-active compound (1) as well as a racemate of compound (1).

The compound of formula (1) In which any one or more $^1$H atoms are replaced by $^2$H(D) atoms is also within the scope of the present invention of formula (1).

The compound of formula (1) and a pharmaceutically acceptable salt thereof may be also in a form of hydrate and/or solvate, thus the compound of the present invention encompasses such hydrate thereof and solvate thereof such as ethanolate. In addition, the compound of the present invention also includes various embodiments of its crystal form.

The pharmaceutically acceptable salt of the compound of formula (1), when the compound has an acidic group, includes, for example, alkali metal salts such as sodium salt and potassium salt; alkaline earth metal salts such as calcium salt and magnesium salt; inorganic metal salts such as zinc salt; and organic base salts such as triethylamine, triethanolamine, tri (hydroxymethyl)aminomethane, and basic amino acid.

The pharmaceutically acceptable salt of the compound of formula (1), when the compound has a basic group, includes, for example, inorganic acid salts such as hydrochloride, hydrobromide, sulfate, phosphate, and nitrate; and organic acid salts such as acetate, propionate, succinate, lactate, malate, tartrate, citrate, maleate, fumarate, methanesulfonate, p-toluenesulfonate, benzenesulfonate, ascorbate, and acidic amino acid.

Preferred salts of starting materials and intermediates, and salts acceptable as pharmaceutical drug substances may be conventional salts. These salts include, for example, acid addition salts like organic acid salts (such as acetate, trifluoroacetate, maleate, fumarate, citrate, tartrate, methanesulfonate, benzenesulfonate, formate, and toluenesulfonate) and inorganic acid salts (such as hydrochloride, hydrobromide, hydroiodide, sulfate, nitrate, and phosphate), salts with amino acids (such as arginine, aspartate, and glutamate), metal salts like alkaline metal salts (such as sodium salt, and potassium salt) and alkaline-earth metal salts (such as calcium salt, and magnesium salt), ammonium salts, and organic base salts (such as trimethylarsine salt, triethylamine salt, pyridine salt, picoline salt, dicyclohexylamine salt, and N,N'-dibenzylethylenediamine salt), or may be suitably selected by a skilled parson.

Processes

Hereinafter, the processes to prepare the compound of the present invention of formula (1) are exemplified along with examples, but the processes to prepare the compound of the present invention should not be limited to the examples. Compounds used in the following process may exist as their salts unless they affect reactions.

The compound of the present invention can be prepared from known compounds as starting materials, for example, by the following methods or similar methods thereto, or optionally in combination with synthetic methods well-known to a person skilled in the art.

In each process illustrated below, any functional groups that need to be protected may be optionally protected, and then may be deprotected after a reaction or a series of reactions are completed to give a desired compound, even though the use of protective groups is not specifically described. The introduction and elimination of protecting groups can be carried out by a method commonly-used in organic synthetic chemistry (for example, see "Protective Groups in Organic Synthesis", 3rd Ed., John Wiley and Sons, inc., New York (1999)), or a similar method.

Process 1

The present compound of formula (1c) can be prepared, for example, by the following process:

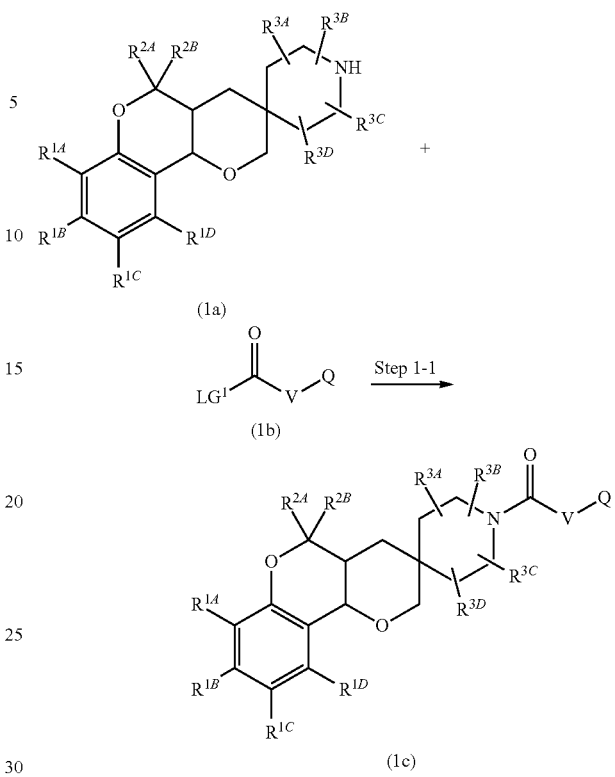

wherein $R^{1A}$, $R^{1B}$, $R^{1C}$, $R^{1D}$, $R^{2A}$, $R^{2B}$, $R^{3A}$, $R^{3B}$, $R^{3C}$, $R^{3D}$, V, and Q are as defined in Item 1, and $LG^1$ denotes a leaving group which includes, for example, halogen atom, and hydroxy.

Compound (1b) can be prepared in a known manner described in, for example, Journal of Medicinal chemistry, 60(15): 6678-6692 (2017), Journal of Medicinal chemistry, 60 (22): 9376-9392 (2017), etc. or in a similar manner thereto, or is commercially available.

Step 1-1

Compound (1c) can be prepared by reacting Compound (1a) prepared in the process below with Compound (1b) such as a carboxylic acid compound and an acid chloride compound in the presence or absence of an appropriate condensation agent and/or an appropriate base in an appropriate solvent.

The base used herein includes amines such as triethylamine, diisopropylethylamine, and pyridine; alkaline metal carbonates such as potassium carbonate, sodium carbonate, and sodium bicarbonate; and the like. It includes preferably triethylamine, diisopropylethylamine, and pyridine.

The condensation agent used herein may be suitably selected from condensation agents which are well used in organic synthetic chemistry, which includes preferably 1-ethyl-3-(3-dimethylaminopropyl) carbodiimide hydrochloride, and 1-hydroxybenzotriazole.

The solvent used herein should not be limited unless the solvent reacts under the reaction condition of the present step, but it includes, for example, ether solvents such as diethyl ether, diisopropyl ether, tetrahydrofuran, methylcyclopentyl ether, anisole, and 1,4-dioxane; aromatic hydrocarbon solvents such as benzene, toluene, chlorobenzene, and xylene; ester solvents such as ethyl acetate, and methyl acetate; aprotic solvents such as N,N-dimethylformamide, N,N-dimethylacetamide, N-methyl-2-pyrrolidinone, 1,3-dimethyl-2-imidazolidinone, acetonitrile, and dimethylsulfoxide; and a mixture thereof. The solvent includes, preferably, tetrahydrofuran, toluene, N,N-dimethylformamide, and acetonitrile.

The reaction time is generally 5 minutes to 72 hours, preferably 30 minutes to 24 hours.

The reaction temperature is generally −78° C. to 200° C., preferably −78° C. to 80° C.

Process 2

The present compound of formula (1c) can be also prepared, for example, by the following process:

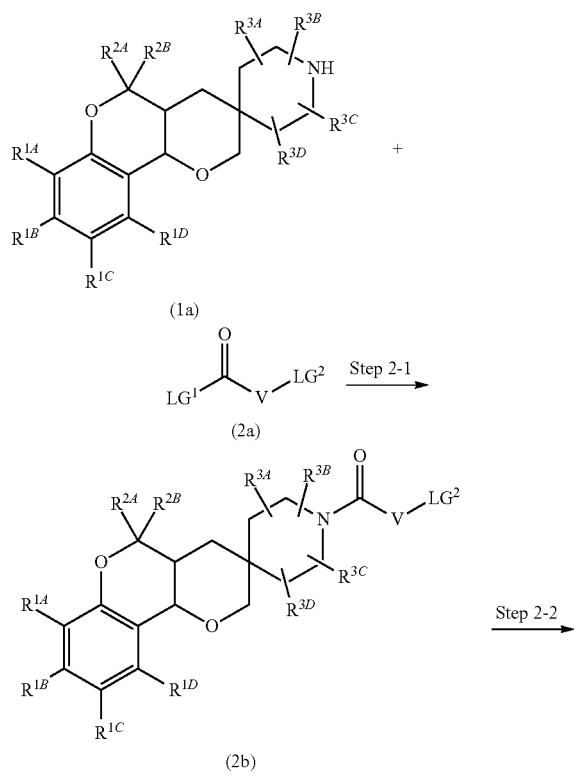

wherein $R^{1A}$, $R^{1B}$, $R^{1C}$, $R^{1D}$, $R^{2A}$, $R^{2B}$, $R^{3A}$, $R^{3B}$, $R^{3C}$, $R^{3D}$, V, and Q are as defined in Item 1, $LG^1$ is as defined in Process 1, and $LG^2$ denotes a leaving group which includes, for example, halogen atom, methanesulfonyloxy, ethanesulfonyloxy, p-toluenesulfonyloxy, and trifluoromethanesulfonyloxy.

Compound (2a) can be prepared in a known manner described in, for example, ACS chemical biology, 12 (8): 2124-2131 (2017), etc. or in a similar manner thereto, or is commercially available.

Step 2-1

Compound (2b) can be prepared from Compound (1a) prepared in the process below and Compound (2a), according to the method described in Step 1-1 in Process 1, or a similar method.

Step 2-2

Compound (1c) can be prepared by reacting Compound (2b) and an imidazole derivate (QH) in the presence or absence of an appropriate base in an appropriate solvent.

The base used herein includes, for example, organic bases such as triethylamine, diisopropylethylamine, tributylamine, 1,5-diazabicyclo[4.3.0]non-5-ene (DBN), 1,8-diazabicyclo[5.4.0]undec-7-ene (DBU), pyridine, dimethylaminopyridine, picoline, and N-methylmorpholine (NMM), and inorganic bases such as sodium bicarbonate, potassium bicarbonate, sodium carbonate, potassium carbonate, cesium carbonate, sodium hydroxide, and potassium hydroxide. It includes preferably triethylamine, diisopropylethylamine, and potassium carbonate.

The solvent used herein should not be limited unless the solvent reacts under the reaction condition of the present step, but it includes, for example, ether solvents such as diethyl ether, diisopropyl ether, tetrahydrofuran, methylcyclopentyl ether, anisole, 1,4-dioxane; aromatic hydrocarbon solvents such as benzene, toluene, chlorobenzene, and xylene; ester solvents such as ethyl acetate, and methyl acetate; aprotic solvents such as N,N-dimethylformamide, N,N-dimethylacetamide, N-methyl-2-pyrrolidinone, 1,3-dimethyl-2-imidazolidinone, acetonitrile, and dimethylsulfoxide; and a mixture thereof. The solvent includes, preferably, tetrahydrofuran, toluene, N,N-dimethylformamide, and acetonitrile.

The reaction temperature is generally −80° C. to reflux temperature, preferably 25° C. to 9t° C.

The reaction time is generally 30 minutes to 48 hours, preferably 6 to 12 hours.

Process 3

The compound of formula (3b) can be prepared, for example, by the following process:

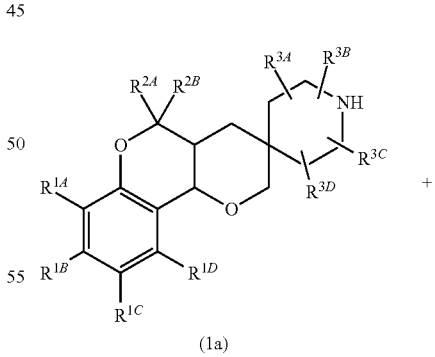

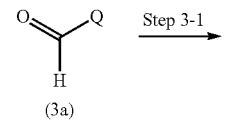

-continued

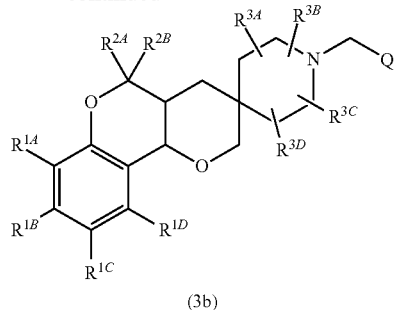

(3b)

wherein $R^{1A}$, $R^{1B}$, $R^{1C}$, $R^{1D}$, $R^{2A}$, $R^{2B}$, $R^{3A}$, $R^{3B}$, $R^{3C}$, $R^{3D}$, and Q are as defined in Item 1.

Compound (3a) can be prepared in a known manner described in, for example, RSC Advances, 4(76): 40561-40568 (2014), Journal of the American Chemical Society, 117(43): 30605-10613 (1995), etc. or in a similar manner thereto, or is commercially available.

Step 3-1.

Compound (3b) can be prepared from Compound (1a) and Compound (3a) in a known manner described in, for example, Journal of the American Chemical Society, 93(12): 2897-2904 (1971), Journal of Organic Chemistry, 37(100): 1673-1674 (1972), Journal of Organic Chemistry, 61(11): 3849-3862 (1996), Tetrahedron, 60: 7899-7906 (2004), etc. or in a similar manner thereto.

Process 4

The compound of formula (4b) can be prepared, for example, by the following process:

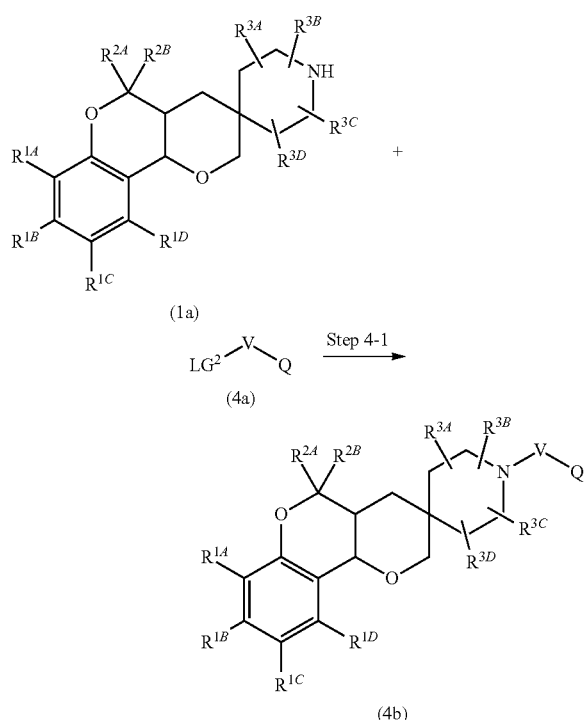

wherein $R^{1A}$, $R^{1B}$, $R^{1C}$, $R^{1D}$, $R^{2A}$, $R^{2B}$, $R^{3A}$, $R^{3B}$, $R^{3C}$, $R^{3D}$, V, and Q are as defined in Item 1, and $LG^2$ is as defined in Process 2.

Compound (4a) can be prepared in a known manner described in, for example, Journal of Medicinal Chemistry, 39(19): 3806-3813 (1996), Advanced Synthesis & Catalysis, 356(9), 1955-1961 (2014), etc. or in a similar manner thereto, or is commercially available.

Step 4-1

Compound (4b) can be prepared from Compound (1a) prepared in the process below and Compound (4a), according to the method described in Step 2-2 in Process 2, or a similar method.

Process 5

The compound of formula (5c) can be prepared, for example, by the following process:

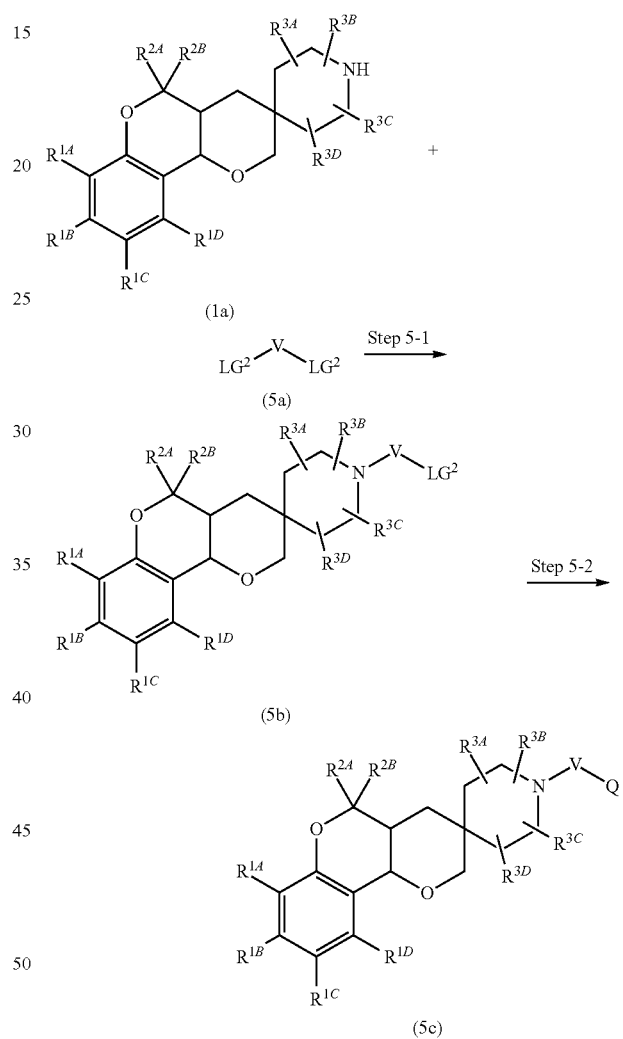

wherein $R^{1A}$, $R^{1B}$, $R^{1C}$, $R^{1D}$, $R^{2A}$, $R^{2B}$, $R^{3A}$, $R^{3B}$, $R^{3C}$, $R^{3D}$, V, and Q are as defined in Item 1, and $LG^2$ is independently as defined in Process 2.

Compound (5a) can be prepared in a known manner described in, for example, Journal of Organic Chemistry, 25: 24-26 (1960), etc. or in a similar manner thereto, or is commercially available.

Step 5-1

Compound (5b) can be prepared from Compound (1a) prepared in the process below and Compound (5a), according to the method described in Step 2-1 in Process 2, or a similar method.

Step 5-2

Compound (5c) can be prepared from Compound (5b) and Compound Q, according to the method described in Step 2-2 in Process 2, or a similar method.

Process 6

The production intermediate of formula (1a) can be prepared, for example, by the following process:

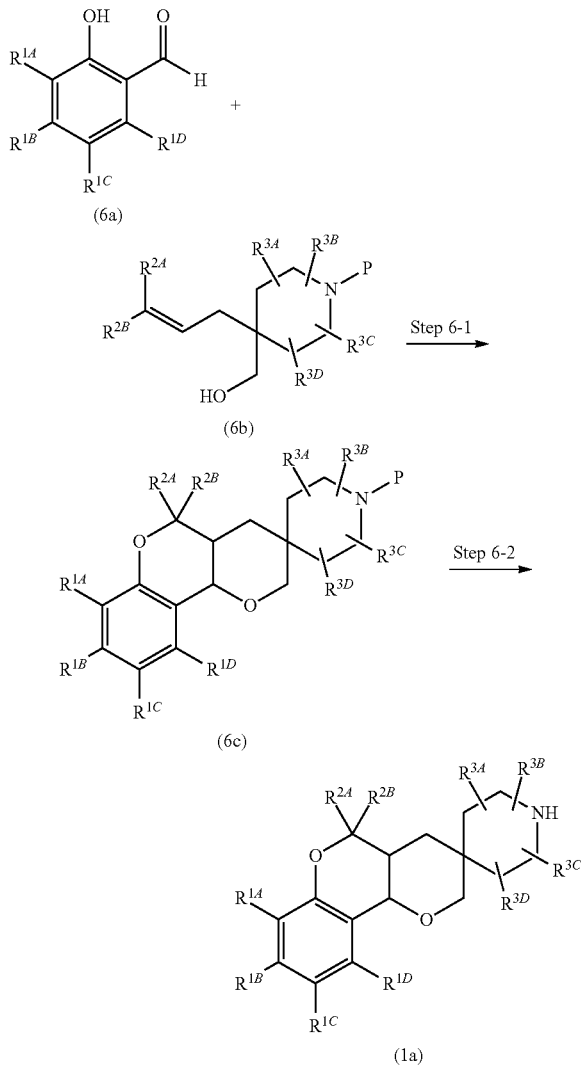

wherein $R^{1A}$, $R^{1B}$, $R^{1C}$, $R^{1D}$, $R^{2A}$, $R^{2B}$, $R^{3A}$, $R^{3B}$, $R^{3C}$, and $R^{3D}$ are as defined in Item 1, and P is an amino-protecting group which includes amino-protecting groups described in Protective Groups in Organic Synthesis (edited by Theodora W. Greene, Peter G. M. Wuts, issued by John Wiley & Sons, Inc. (1999).

Step 6-1

Compound (6c) can be prepared from commercially-available Compound (6a) and Compound (6b) obtained in the process shown below in a known manner described in, for example, Journal of the Chemical Society, Perkin Transactions 1, (0.11): 1401-1404 (2002), Chemistry Letters, (10): 889-890 (1996), Journal of Organic Chemistry, 64 (26): 9507-9511 (1999), Synthesis, 44 (23), 3579-3589 (2012), Tetrahedron Letters, 54(28), 3639-3642 (2013), Synlett, 26(15), 2151-2155 (2015), Organic Letters, 3(17), 2669-2672 (2001), etc. or in a similar manner thereto.

Step 6-2

Compound (1a) can be prepared by deprotecting the protecting group a in Compound (6c). The present step may be carried out according to, for example, Protective Groups in Organic Synthesis (edited by Theodora W. Greene, Peter G. M. Wuts, issued by John Wiley & Sons, Inc., 1999).

Process 7

The production intermediate of formula (6b) can be prepared, for example, by the following process:

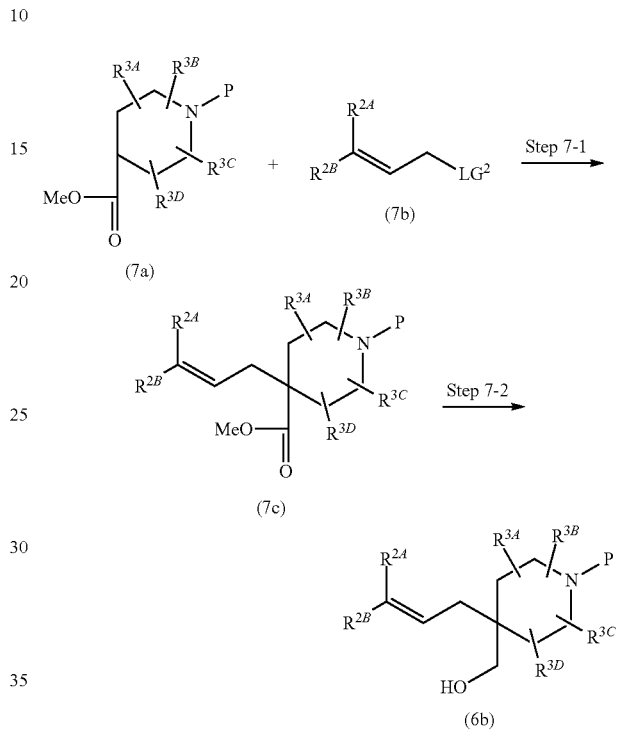

wherein $R^{2A}$, $R^{2B}$, $R^{3A}$, $R^{3B}$, $R^{3C}$, and $R^{3D}$ are as defined in Item 1, P is as defined in Process 6, and $LG^2$ is as defined in Process 2.

Step 7-1

Compound (7c) can be prepared from commercially-available Compound (7a) and commercially-available Compound (7b) in a known manner described in, for example, Journal of the American Chemical Society, 137(46): 14590-14593 (2015), European Journal of Medicinal Chemistry, 45(7): 2827-2840 (2010), Bioorganic & Medicinal Chemistry Letters, 14(14): 3675-3678 (2004), Bioorganic & Medicinal Chemistry Letters, 13 (13): 2167-2172 (2003), Synthesis, (20): 3241-3246 (2011), Bioorganic & Medicinal Chemistry Letters, 20(22): 6375-6378 (2010), etc. or in a similar manner thereto.

Step 7-2

Compound (6b) can be prepared from Compound (7c) in a known manner described in, for example, Bioorganic & Medicinal Chemistry Letters, 25(22): 5032-5035 (2015), Bioorganic & Medicinal Chemistry Letters, 14(17): 4453-4459 (2004), Angewandte Chemie, International Edition, 56(4), 1152-1157 (2017), Tetrahedron Letters, 51(49), 6415-6417 (2010), Organic Process Research & Development, 17(2): 257-264 (2013), etc. or in a similar manner thereto.

The compound of the present invention which has desired substituents at desired positions can be given by suitably combining the above processes. The intermediates and desired compounds in the above processes may be isolated/purified by a purification generally-used in organic chemistry, for example, filtration, extraction, washing, drying, concentration, crystallization, various chromatography, etc. or a combination thereof. Some intermediates may be used in next step without any purification.

The starting compounds or intermediates in the above processes can exist in salt form such as hydrochloride, or directly in free form, depending on reaction condition, etc. If it is necessary to use free form of a starting compound or intermediate in salt form, the salt form can be dissolved or suspended in an appropriate solvent and neutralized with a base such as aqueous sodium bicarbonate, or an acid to be transformed to its free form.

The compound of formula (1) or a pharmaceutically acceptable salt thereof may sometimes exist as tautomer such as keto-enol form, regioisomer, geometric isomer, or optical isomer. All these possible isomers and mixtures thereof in any mixing ratio are also included in the present invention.

Optical isomers can be divided by a known separation step such as a method with optically-active column and a fraction crystallization method, in an appropriate step of the above processes. In addition, an optically active starting material may be used.

If the compound of formula (1) should be obtained as a salt of, when the compound of formula (1) is obtained as a salt, it may be purified without further reaction, and when it is obtained in a free form, it may be dissolved or suspended in an appropriate organic solvent and an acid or base may be added therein to form a salt. The compound of formula (1) or a pharmaceutically acceptable salt thereof may sometimes exist in form of solvate with water or various solvents. Such solvates are also included in the present invention.

The "treatment" used herein means the administration of the active ingredient of the present invention to a person diagnosed with the development of a disease by a doctor (i.e., a patient).

The compound of the present invention can be orally or parenterally administrated directly or as a suitable drug formulation. The dosage form includes, for example, a tablet, a capsule, a powder, a granule, a liquid, a suspension, an injection, a patch, a poultice, and the like, but it is not limited to them. The drug formulation is prepared by a common method using pharmaceutically acceptable additives.

As the additive, an excipient, a disintegrant, a binder, a fluidizer, a lubricant, a coating agent, a solubilizer, a solubilizing adjuvant, a thickener, a dispersant, a stabilizing agent, a sweetening agent, a flavor, and the like may be used, depending on purpose. The additive used herein includes, for example, lactose, mannitol, crystalline cellulose, low-substituted hydroxypropylcellulose, corn starch, partially-pregelatinized starch, carmellose calcium, croscarmellose sodium, hydroxypropylcellulose, hydroxypropylmethylcellulose, polyvinyl alcohol, magnesium separate, sodium stearyl fumarate, polyethylene glycol, propylene glycol, titanium oxide, talc, and the like.

The route of administration should be chosen to be the most effective route for the treatment, which includes oral administration and parenteral administration such as intravenous injection, swabbing, inhalation, and eyedrop. Preferred one is oral administration. The dosage form includes, for example, tablet and injection, and preferably tablet. The dose of the pharmaceutical composition and the frequency of administration thereof can depend on the administration route, and patient's disease, symptom, age, body weight, etc., thus it is impossible to define them flatly. In general, the present compound may be administered to an adult by about 0.0001—about 5000 mg/day, preferably about 0.001—about 1000 mg/day, more preferably about 0.1—about 500 mg, particularly preferably about 1-about 300 mg, which may be administered once a day or a few times a day, preferably once to three times a day.

The compound of the present invention may be used together or combined with a different drug, in order to enhance the effect and/or reduce side effects. The different drug which may be used together or combined with the present compound includes, for example, an anticancer alkylating agent, an anticancer antimetabolite, an anticancer antibiotic, a plant-derived anticancer agent, an anticancer platinum complex compound, an anticancer camptothecin derivative, an anticancer tyrosine kinase inhibitor, an anticancer serine/threonine kinase inhibitor, an anticancer phospholipid kinase inhibitor, an anticancer monoclonal antibody, interferon, a biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicaments, or a pharmaceutically acceptable salt thereof. In more detail, it includes, for example, azacytidine, vorinostat, decitabine, romidepsin, idarubicin, daunorubicin, doxorubicin, enocitabine, cytarabine, mitoxantrone, thioguanine, etoposide, ifosfamide, cyclophosphamide, dacarbazine, temozolomide, nimustine, busulfan, procarbazine, melphalan, ranimustine, all-trans-retinoic acid, tamibarotene, cisplatin, carboplatin, oxaliplatin, irinotecan, bleomycin, mitomycin C, methotrexate, paclitaxel, docetaxel, gemcitabine, tamoxifen, thiotepa, tegafur, fluoruracil, everolimus, temsirolimus, gefitinib, erlotinib, imatinib, crizotinib, osimertinib, afatinib, dasatinib, bosutinib, vandetanib, sunitinib, axitinib, pazopanib, lenvatinib, lapatinib, nilotinib, ibrutinib, ceritinib, alectinib, tofacitinib, baricitinib, ruxolitinib, olaparib, sorafenib, vemurafenib, dabrafenib, trametinib, palbociclib, bortezomib, carfilzomib, rituximab, cetuximab, trastuzumab, bevacizumab, panitumumab, nivolumab, atezolizumab, mogamulizumab, alemtuzumab, ofatumumab, ipilimumab, ramucirumab, brentuximab vedotin, gemtuzumab ozogamicin, and inotuzumab ozogamicin. In addition, the above-mentioned different drug which may be used together with the present compound may be also cellular medicines. The cellular medicines used together includes, for example, CAR-T cell. In more detail, it includes, for example, tisagenlecleucel, and axicabtagene ciloleucel.

The administration interval of the present compound and the different drug used together should not be limited. They may be simultaneously administered to a subject in need thereof, or may be administered with time interval. In addition, the present compound and the different drug may be mixed as a combination drug. The dose of the different drug used together may be defined suitably based on the clinically-used dose. The mixing ratio of the present compound and the different drug used together may be defined suitably depending on subject in need of the treatment, administration route, and subject's disease, symptom, combination, etc. When the subject in need of the treatment is human being, the different drug used together may be used, for example, in a dose of 0.01-100 parts by weight per one part of the present compound.

The protecting groups, condensation agents, etc. used herein are sometimes shown with abbreviations based on IUPAC-IUB, which are conventionally used in this technical field. However, the compound names herein should not be always based on IUPAC nomenclature system.

EXAMPLES

The present invention is explained in more detail in the following by referring to Reference examples, Examples, and Tests; however, the technical scope of the present invention should not be limited thereto. The compound names used in Reference examples and Examples should not be always based on IUPAC nomenclature system.

In the present description, the abbreviations shown below are sometimes used.
Hex: hexane
IPA: isopropyl alcohol
THF: tetrahydrofuran
TFA: trifluoroacetic acid
MeCN: acetonitrile
Me: methyl
Et: ethyl
Pr: propyl
Ph: phenyl
Boc: tert-butoxycarbonyl The NMR data used for identification of compounds were obtained with a JEOL JNM-AL series AL400.

The signs used in NMR denote the following mearings, s is singlet, d is doublet, dd is double doublet, t is triplet, td is triple doublet, q is quartet, m is multiplet, br is broad, brs is broad singlet, brm is broad multiplet, and J is coupling constant.

Analytical conditions of LC/MS used for identification of compounds are shown below. Mass spectrometry values (MS ((m/z)) are shown in $[M+H]^+$ or $[M+2H]^{2+}$, and retention time is shown as Rt (minutes).

LC/MS Analytical Method (Condition 1):
Detection apparatus: ACQUITY™ SQ detector (Waters Corporation)
HPLC: ACQUITY™ UPLC system
Column: Waters ACQUITY™ UPLC BEH C18 (1.7 μm, 2.1 mm×30 mm)
Solvent: A: 0.06% formic acid/$H_2O$, B: 0.06% formic acid/MeCN
Gradient condition: 0.0 to 1.3 minutes linear gradient from B 2% to B 96%
Flow rate: 0.8 mL/min
UV: 220 nm and 254 nm LC/MS Analytical Method (Condition 2):
LCMS-2020 system (Shimadzu Corporation)
Column: Kinetex™ 1.7 μm Minibore column, C18 (30 mm×2.1 mm)
Solvent: A: 0.05% TFA/$H_2O$, B: MeCN
Gradient condition: 0.0 to 1.7 min linear gradient from B 10% to B 99%, 1.9 min B 99%
Flow rate: 0.50 mL/min
UV: 220 nm and 254 nm The optical activities of the present compounds and their synthetic intermediates were analyzed under the following conditions.
HPLC system for optical resolution
Pump: LC-20AD (Shimadzu Corporation)
Detector: SPD-20A (Shimadzu Corporation)
Pump: SIL-20A (Shimadzu Corporation)

Condition A
Column: CHIRALPAK IE
Size: 0.46 cm I.D.×25 cm L
Mobile phase: n-Hex/EtOH/i-PrNH$_2$=90/10/0.1<v/v>
Flow rate: 1.0 mL/min
Temperature: 40° C.
Wave length: 287 nm Condition B
Column: CHIRALPAK IE
Size: 0.46 cm I.D.×25 cm L
Mobile phase: n-Hex/IPA/i-PrNH$_2$=80/20/0.1<v/v>
Flow rate: 1.0 mL/min
Temperature: 40° C.
Wave length: 285 nm Condition C
Column: CHIRALPAK IE
Size: 0.46 cm I.D.×25 cm L
Mobile phase: MeOH/i-PrNH$_2$=100/0.1<v/v>
Flow rate: 1.0 mL/min
Temperature: 40° C.
Wave length: 280 nm Condition D
Column: CHIRALPAK AD-H
Size: 0.46 cm I.D.×25 cm L
Mobile phase: n-Hex/IPA/EtOH/i-PrNH$_2$=85/5/10/0.1<v/v>
Flow rate: 1.0 mL/min
Temperature: 40° C.
Wave length: 280 nm Condition E
Column: CHIRALPAK AD-H
Size: 0.46 cm I.D.×25 cm L
Mobile phase: MeOH/Et$_2$NH=100/0.1<v/v>
Flow rate: 1.0 mL/min
Temperature: 40° C.
Wave length: 280 nm Reference Example 1 tert-Butyl 4-(hydroxymethyl)-4-(3-methylbut-2-en-1-yl) piperidine-1-carboxylate

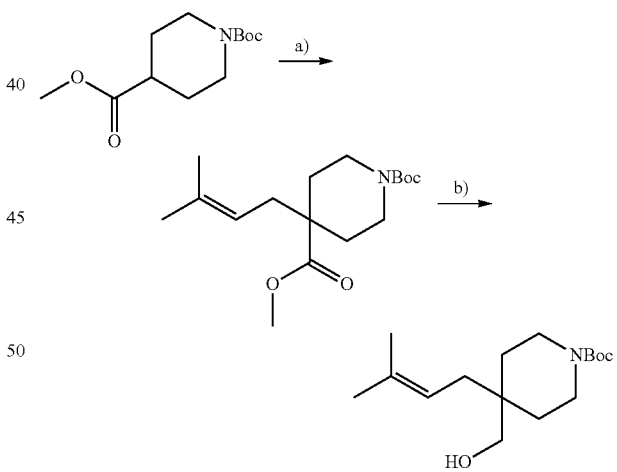

Reference example 1 a) Preparation of 1-tert-butyl 4-methyl 4-(3-methylbut-2-en-1-yl)piperidine-1,4-dicarboxylate To a solution of 1-tert-butyl 4-methyl piperidine-1,4-dicarboxylate (69.0 g) in tetrahydrofuran (700 mL) was added dropwise 1 mol/L sodium bis(trimethylsilyl)amide (326 mL) at −78° C., and the reaction mixture was stirred at the temperature for an hour. The reaction mixture was warmed to −20° C., and stirred at the temperature for an hour. To the reaction mixture was added dropwise 1-bromo-3-methyl-2-butene (42.6 mL) at −78° C. The reaction mixture was warmed to −20° C., and stirred at the temperature for 3 hours. The reaction mixture was warmed to room temperature, and stirred overnight. After completing the reaction, aqueous ammonium chloride was added to the reaction mixture. Then, water and ethyl acetate were added thereto. The mixture was separated into ethyl acetate layer and water layer in a separating funnel. The obtained organic layer was washed with brine, dried over sodium sulfate. The solvent was removed in vacuo, and the obtained residue was purified by silica gel column chromatography (hexane/ethyl acetate) to give the title compound (69.0 g).

$^1$H-NMR (400 MHz, CDCl$_3$): 5.01 (1H, t, J=7.5 Hz), 3.87-3.72 (2H, m), 3.68 (3H, s), 2.86 (2H, dd, J=2.7, 11.4 Hz), 2.21 (2H, d, J=7.3 Hz), 2.06 (2:1, d, J=14.2 Hz), 1.69 (3H, s), 1.58 (3H, s), 1.44 (9H, s), 1.43-1.34 (2H, m).

LC-MS (Condition 1); [M+H]$^+$ 312.3/Rt (min.) 1.24 b) Preparation of tert-butyl 4-(hydroxymethyl)-4-(3-methylbut-2-en-1-yl)piperidine-1-carboxylate (Reference example 1)

To a solution of lithium aluminium hydride (9.25 g) in tetrahydrofuran (700 mL) was added dropwise a solution of 1-tert-butyl 4-methyl 4-(3-methylbut-2-en-1-yl)piperidine-1,4-dicarboxylate (69.0 g) which was obtained in Step a) in tetrahydrofuran (300 mL) at −78° C. The reaction mixture was stirred at the temperature for an hour. The reaction mixture was stirred at −20° C. under a nitrogen atmosphere for 5 hours. After completing the reaction, saturated aqueous sodium sulfate was added to the reaction mixture at 0° C. The mixture was stirred at room temperature for an hour, and dried over magnesium sulfate. The reaction mixture was filtrated with Celite, and the solvent of the filtrate was removed in vacuo. The obtained residue was purified by silica gel column chromatography (hexane/ethyl acetate) to give Reference example 1 (58.0 g).

$^1$H-NMR (400 MHz, CDCl$_3$): 5.17 (1H, t, J=7.8 Hz), 3.48-3.41 (2H, m), 3.46 (2H, s), 3.38-3.31 (2H, m), 2.09 (2H, d, J=7.8 Hz), 1.73 (3H, s), 1.65 (3H, s), 1.51-1.37 (4H, m), 1.46 (9H, s).

LC-MS (Condition 1); [M+H]$^+$ 284.3/Rt (min.) 1.08

Reference Example 2

Racemate of (4'aR,10'bR)-9'-chloro-5',5'-dimethyl-4'a,10'b-dihydro-2'H,4'H,5'H-spiro[piperidine-4,3'-pyrano[3,2-c][1]benzofuran] and (4'aS,10'bS)-9'-chloro-5',5'-dimethyl-4'a,10'b-dihydro-2'H,4'H,5'H-spiro[piperidine-4,3'-pyrano[3,2-c][1]benzofuran]

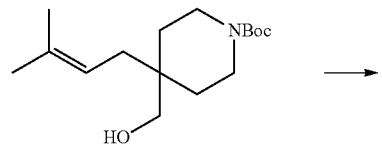

Reference example 1

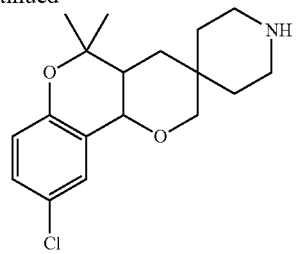

Reference example 2

To a solution of Reference example 1 (69.0 g) in dichloromethane (1000 ML) were added 5-chloro-2-hydroxybenzaldehyde (48.0 g), trimethyl orthoformate (100 mL), and then p-toluenesulfonic acid monohydrate (1.90 g) at 0° C., and the reaction mixture was stirred at 0° C. under a nitrogen atmosphere for 5 hours. The solvent was removed in vacuo, and 4 mcl/L hydrochloric acid in ethyl acetate (300 mL) was added to the obtained residue at 0° C. The mixture was stirred at 0° C. for an hour. The solvent was removed in vacuo, and the obtained residue was purified by amine silica gel column chromatography (chloroform/methanol) to give a racemate of Reference example 2 (61.5 g).

$^1$H-NMR (400 MHz, CDCl$_3$): 7.38 (1H, s), 7.11 (1H, d, J=8.6 Hz), 6.70 (1H, d, J=8.6 Hz), 4.12 (1H, d, J=11.4 Hz), 4.08 (1H, d, J=10.9 Hz), 3.31 (1H, d, J=10.9 Hz), 2.90-2.86 (3H, m), 2.81-2.77 (1H, m), 1.91-1.80 (3H, m), 1.57-1.53 (1H, m), 1.39-1.37 (2H, m), 1.38 (3H, s), 1.17 (3H, s), 1.11-1.05 (1H, m).

LC-MS (Condition 1); [M+H]$^+$ 322.2/Rt (min.) 0.77

The obtained Reference example 2 was optically resolved to obtain Reference example 3 and Reference example 4 which are optical active compounds of Reference example 2.

Reference Example 3

Condition A; Rt (min.)=10.35
LC-MS (Condition 1); [M+H]$^+$ 322.2/Rt (min.) 0.77

Reference Example 4

Condition A; Rt (min.)=12.07
LC-MS (Condition 1); [M+H]$^+$ 322.2/Rt (min.) 0.77

Reference Examples 5-15

Reference examples 5 to 15 shown in the following table were prepared from each corresponding starting compound in the manner of Reference example 2.

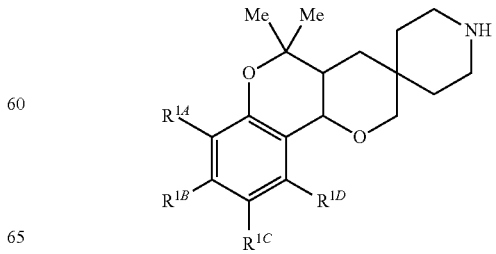

| Reference example | $R^{1A}$ | $R^{1B}$ | $R^{1C}$ | $R^{1D}$ | Racemic or Chiral | Rt (min) (Condition) | LC – MS (Condition 1) $[M + H]^+$/Rt (min) |
|---|---|---|---|---|---|---|---|
| 5 | Cl | H | H | H | Racemic | — | 322.5/0.72 |
| 6 | Br | H | H | H | Racemic | — | 366.2/0.74 |
| 7 | H | Cl | H | H | Racemic | — | 322.5/0.75 |
| 8 | H | Cl | H | H | Chiral | 8.09 (Condition C) | 322.5/0.74 |
| 9 | H | Cl | H | H | Chiral | 11.27 (Condition C) | 322.5/0.76 |
| 10 | H | Br | H | H | Racemic | — | 366.2/0.77 |
| 11 | H | H | F | H | Racemic | — | 306.5/0.65 |
| 12 | H | H | F | H | Chiral | 6.07 (Condition B) | 306.5/0.63 |
| 13 | H | H | F | H | Chiral | 7.35 (Condition B) | 306.5/0.65 |
| 14 | H | H | Br | H | Racemic | — | 366.2/0.75 |
| 15 | H | H | $N_3$ | H | Racemic | — | 329.3/0.78 |

The NMR data of Reference examples 5, 6, 7, 10, 11, and 14 shown in the above table are shown below.

Reference Example 5

$^1$H-NMR (400 MHz, DMSO-d6): 7.28 (1H, d, J=7.3 Hz), 7.27 (1H, d, J=6.7 Hz), 6.84 (1H, dd, J=7.3, 7.9 Hz), 4.17 (1H, d, J=11.0 Hz), 3.94 (1H, d, J=11.0 Hz), 3.34-3.27 (1H, m), 2.69-2.58 (4H, m), 1.82-1.74 (2H, m), 1.55-1.51 (1H, m), 1.41-1.37 (1H, m), 1.37 (3H, s), 1.24-1.22 (2H, m), 1.15 (3H, s), 1.10-1.06 (1H, m).

Reference Example 6

$^1$H-NMR (400 MHz, DMSO-d6): 7.42 (1H, d, J=7.6 Hz), 7.31 (1H, d, J=8.0 Hz), 6.79 (1H, dd, J=7.6, 7.9 Hz), 4.18 (1H, d, J=11.2 Hz), 3.94 (1H, d, J=10.8 Hz), 3.29 (2H, d, J=11.2 Hz), 2.65-2.60 (4H, m), 1.81-1.76 (2H, m), 1.54-1.51 (1H, m), 1.43-1.38 (1H, m), 1.37 (3H, s), 1.24-1.21 (2H, m), 1.15 (3H, s), 1.15-1.10 (1H, m).

Reference Example 7

$^1$H-NMR (400 MHz, CDCl$_3$): 7.33 (1H, d, J=9.2 Hz), 6.88 (1H, d, J=8.4 Hz), 6.80 (1H, s), 4.14-4.07 (2H, m), 3.32 (1H, d, J=11.6 Hz), 2.90-2.80 (4H, m), 1.93-1.82 (2H, m), 1.58-1.51 (1H, m), 1.38-1.34 (1H, m), 1.36 (3H, s), 1.27-1.19 (2H, m), 1.24 (3H, s), 1.12-1.06 (1H, m).

Reference Example 10

$^1$H-NMR (400 MHz, DMSO-d6): 7.23 (1H, d, J=8.8 Hz), 7.01 (1H, d, J=8.4 Hz), 6.91 (1H, s), 4.09 (1H, d, J=10.4 Hz), 3.94 (1H, d, J=11.6 Hz), 3.28 (1H, d, J=11.6 Hz), 2.64-2.57 (4H, m), 1.80-1.69 (2H, m), 1.54-1.50 (1H, m), 1.40-1.35 (1H, m), 1.32 (3H, s), 1.22-1.21 (21H, m), 1.13 (3H, s), 1.11-1.04 (1H, m).

Reference Example 1

$^1$H-NMR (400 MHz, DMSO-d6): 7.03-6.94 (2H, m), 6.24-6.70 (1H, m), 4.12 (1H, d, J=11.2 Hz), 3.95 (1H, d, J=12.8 Hz), 3.27 (1H, d, J=11.6 Hz), 2.64-2.57 (4H, m), 1.80-1.69 (2H, m), 1.54-1.51 (1H, m), 1.41-1.37 (1H, m), 1.31 (3H, s), 1.22-1.21 (2H, m), 1.13 (3H, s), 1.07-1.04 (1H, m).

Reference Example 14

$^1$H-NMR (400 MHz, DMSO-d6): 7.37 (1H, d, J=2.4 Hz), 7.27 (1H, d, J=9.2 Hz), 6.69 (1H, d, J=9.2 Hz), 4.14 (1H, d, J=10.8 Hz), 3.95 (1B, d, J=10.8 Hz), 3.28 (1H, d, J=11.2 Hz), 2.64-2.57 (4H, m), 1.80-1.68 (2H, m), 1.54-1.50 (1H, m), 1.40-1.35 (1H, m), 1.32 (3H, s), 1.22-1.21 (2H, m), 1.12 (3H, s), 1.11-1.04 (1H, m).

Reference Example 16

Racemate of 1-[(4'aS,10'bS)-9'-chloro-5',5'-dimethyl-4'a,10'b-dihydro-2'H,4'H,5'H-spiro[piperidine-4,3'-pyrano[3,2-c][1]benzopyran]-1-yl]-2-chloroethan-1-one and 1-[(4'aR,10'bR)-9'-chloro-5',5'-dimethyl-4'a,10'b-dihydro-2'H,4'H,5'H-spiro[piperidine-4,3'-pyrano[3,2-c][1]benzopyran]-1-yl]-2-chloroethan-1-one

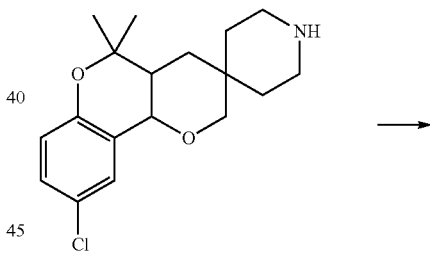

Reference example 2

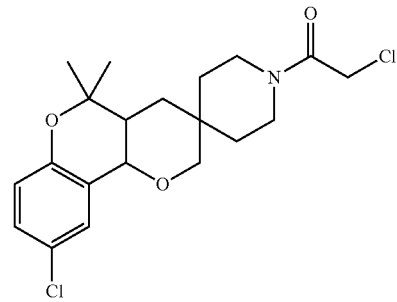

Reference example 16

To a solution of Reference example 2 (2.00 g) in tetrahydrofuran (150 mL) were added potassium carbonate (4.30 g), and then chloroacetyl chloride (0.7 mL) at 0° C., and the reaction mixture was stirred at 0° C. under a nitrogen atmosphere for 2 hours. The reaction mixture was filtrated with Celite, and the solvent was removed in vacuo. The obtained residue was purified by silica gel column chromatography (hexane/ethyl acetate) to give Reference example 16 (2.05 g).

¹H-NM. (400 MHz, CDCl₃): 7.37 (1H, s), 7.13 (1H, d, J=8.7 Hz), 6.70 (1H, d, J=8.7 Hz), 4.12-4.05 (4H, m), 3.85-3.76 (1H, m), 3.60-3.36 (4H, m), 1.90-1.84 (2H, m), 1.79-1.74 (1H, m), 1.66-1.57 (1H, m), 1.49-1.40 (2H, m), 1.36 (3H, s), 1.17 (3H, s), 1.15-1.10 (1H, m).

LC-MS (Condition 1); [M+H]⁺ 398.2/Rt (min.) 1.17

Reference Example 17 tert-Butyl 4-(hydroxymethyl)-4-(prop-2-yn-1-yl) piperidine-1-carboxylate

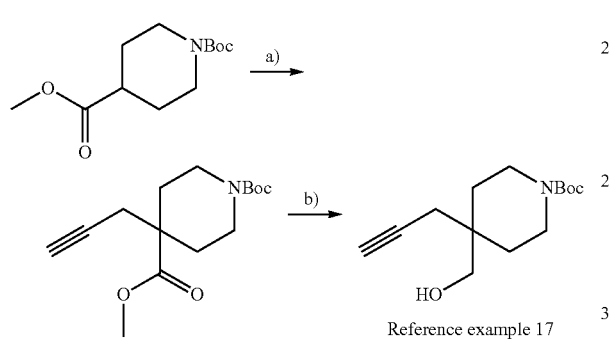

Reference example 17 a) Preparation of 1-tert-butyl 4-methyl 4-(prop-2-yn-1-yl)piperidine-1,4-dicarboxylate A solution of 1-tert-butyl 4-methyl piperidine-1,4-dicarboxylate (1.00 g) in THF (24.0 mL) was cooled to −78° C. To the cooled solution was added 1.0 mol/L sodium hexamethyldisilazide in THF (8.22 mL), and the reaction mixture was stirred at −78° C. for 30 minutes, and then at −18° C. for 45 minutes. The reaction mixture was cooled to −78° C., and then propargyl bromide (0.62 mL) was added dropwise thereto. The reaction mixture was gradually warmed from −78° C. to −20° C., and then saturated aqueous ammonium chloride was added thereto. The mixture was extracted with ethyl acetate twice, and the obtained organic layer was dried over anhydrous sodium sulfate. The mixture was filtrated, and the solvent of the filtrate was removed in vacuo. The obtained residue was purified by silica gel column chromatography (chloroform/methanol) to give the title compound (982 mg).

LC-MS (Condition 1); [M+H]⁺ 282.3/Rt (min.) 1.02 b) Preparation of tert-butyl 4-(hydroxymethyl)-4-(prop-2-yn-1-yl)piperidine-1-carboxylate (Reference example 17)

A solution of the compound obtained in Step a) (928 mg) in a mixture of methanol (8.2 mL) and THE (9.2 mL) was heated to 55° C. To the heated solution was added sodium borohydride (449 mg), and the reaction mixture was stirred for an hour. Additional sodium borohydride (449 mg) was added thereto, and the reaction mixture was stirred for 3 hours. The reaction solution was diluted with water. The mixture was extracted with ethyl acetate three times, and the obtained organic layer was dried over anhydrous sodium sulfate. The mixture was filtrated, and the solvent of the filtrate was removed in vacuo. The obtained residue was purified by silica gel column chromatography (hexane/ethyl acetate) to give Reference example 17 (515 mg).

LC-MS (Condition 1); [M+H]⁺ 254.3/Rt (min.) 0.84

Reference Example 18

A mixture of tert-butyl 4-(hydroxymethyl)-4-[(2E)-3-(phenylsulfanyl) prop-2-en-?-yl]piperidine-1-carboxylate and tert-butyl 4-(hydroxymethyl)-4-[(2Z)-3-(phenylsulfanyl)prop-2-en-1-yl]piperidine-1-carboxylate

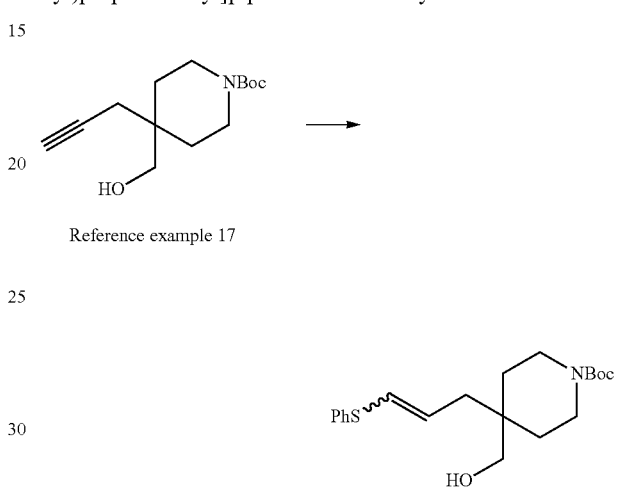

Reference example 18

A solution of Reference example 17 (515 mg), azobisisobutyronitrile (100 mg), and benzenethiol (207 μL) in toluene (10 mL) was stirred at 80° C. under a nitrogen atmosphere for an hour. The reaction solution was concentrated in vacuo, and the obtained residue was purified by silica gel column chromatography (hexane/ethyl acetate) to give Reference example 18 (498 mg).

LC-MS (Condition 1); [M+H]⁺ 364.3/Rt (min.) 1.17

Reference Example 19

Racemate of tert-butyl (4'aS,10'bS)-8'-chloro-5'-(phenylsulfanyl)-4'a,10'b-dihydro-2'H,4'H,5'H-spiro[piperidine-4,3'-pyrano[3,2-c][1]benzopyran]-1-carboxylate and tert-butyl (4'aR,10'bR)-8'-chloro-5'-(phenylsulfanyl)-4'a,10'b-dihydro-2'H,4'H,5'H-spiro[piperidine-4,3'-pyrano[3,2-c][1]benzopyran]-1-carboxylate

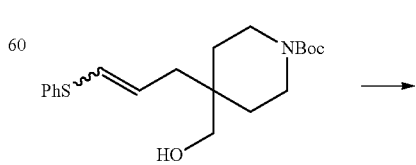

Reference example 18

-continued

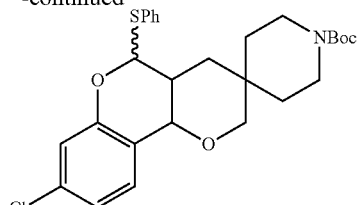

Reference example 19

A solution of Reference example 18 (479 mg), trimethyl orthoformate (288 μL), and p-toluenesulfonic acid monohydrate (12.5 mg) in dichloromethane (6.6 mL) was stirred at 0° C. 4-Chloro-2-hydroxybenzaldehyde (411 mg) was added thereto, and the mixture was stirred at room temperature overnight. The reaction solution was concentrated in vacuo, and the obtained residue was purified by amino column chromatography (chloroform) to give Reference example 19 (691 mg).

LC-MS (Condition 1); [M+H]$^+$ 446.3/Rt (min.) 1.45

Reference Example 20

Racemate of tert-butyl (4'aS,10'bR)-8'-chloro-4'a, 10'b-dihydro-2'H,4'H,5'H-spiro[piperidine-4,3'-pyrano[3,2-c][1]benzopyran]-1-carboxylate and text-butyl (4'aR,10'bS)-8'-chloro-4'a,10'b-dihydro-2'H,4'H,5'H-spiro[piperidine-4,3'-pyrano[3,2-c][1]benzopyran]-1-carboxylate

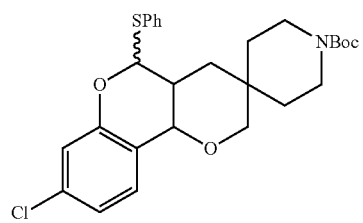

Reference example 19

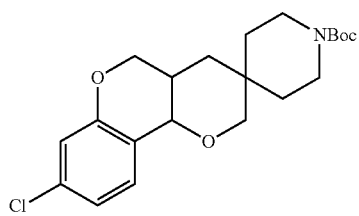

Reference example 20

A solution of Reference example 19 (309 mg), azobisisobutyronitrile (10 mg), and tributyltin hydride (489 μL) in toluene (6.2 mL) was stirred at 100° C. under a nitrogen atmosphere for an hour. The reaction solution was concentrated in vacuo, and the obtained residue was purified by silica gel column chromatography (hexane/ethyl acetate) to give Reference example 20 (167 mg).

LC-MS (Condition 1); [M+H]$^+$ 338.3/Rt (min.) 1.35

Reference Example 21

Racemate of (4'aR,10'bS)-8'-chloro-4'a,10'b-dihydro-2'H,4'H,5'H-spiro[piperidine-4,3'-pyrano[3,2-c][1]benzopyran] and (4'aS,10'bR)-8'-chloro-4'a, 10'b-dihydro-2'H,4'H,5'H-spiro[piperidine-4,3'-pyrano[3,2-c][1]benzopyran]

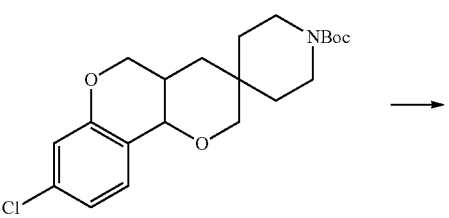

Reference example 20

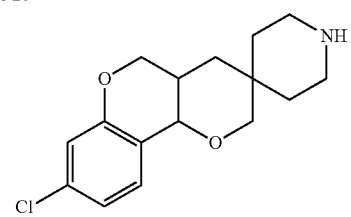

Reference example 21

A solution of Reference example 20 (167 mg) in 4 mol/L hydrochloric acid/dioxane (1.7 mL) was stirred at 70° C. for 30 minutes. The reaction solution was concentrated in vacuo, and the obtained residue was purified by amino column chromatography (chloroform/methanol) to give Reference example 21 (105 mg).

LC-MS (Condition 1); [M+H]$^+$ 294.3/Rt (min.) 0.70

Example 1

Racemate of 1-[(4'aS,10'bS)-9'-chloro-5',5'-dimethyl-4'a,10'b-dihydro-2'H,4'H,5'-spiro[piperidine-4, 3'-pyrano[3,2-c][1]benzopyran]-1-yl]-2-(2-methyl-1H-imidazol-1-yl)ethan-1-one and 1-[(4'aR,10'bR)-9'-chloro-5',5'-dimethyl-4'a,10'b-dihydro-2'H,4'H, 5'H-spiro[piperidine-4,3'-pyrano[3,2-c][1] benzopyran]-1-yl]-2-(2-methyl-1H-imidazol-1-yl) ethan-1-one

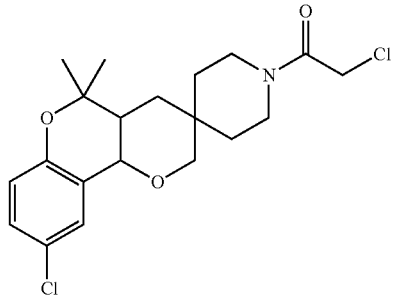

Reference example 16

Example 1

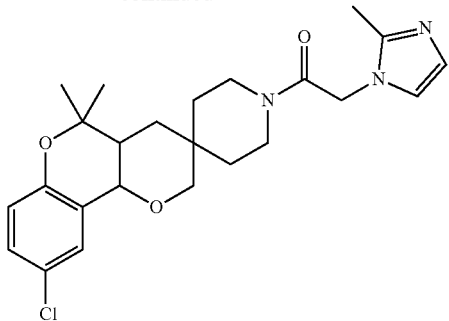

To a solution of Reference example 16 (2.0 g) in tetrahydrofuran (50 mL) were added potassium carbonate (4.0 g) and 2-methyl-1H-imidazole (1.53 g), and the reaction mixture was stirred at 60° C. for 2 hours. The reaction solution was filtrated with Celite, and the solvent was removed in vacuo, and the obtained residue was purified by silica gel column chromatography (hexane/ethyl acetate) to give Example 1. (2.05 g).

$^1$H-NMR (400 MHz, CDCl$_3$): 7.36 (1H, s), 7.10 (1H, d, J=8.8 Hz), 6.97-6.90 (1H, m), 6.83-6.75 (1H, m), 6.70 (1H, d, J=8.7 Hz), 4.65 (2H, s), 4.11-4.06 (2H, m), 3.85-3.76 (1H, m), 3.47-3.36 (4H, m), 2.34 (3H, s), 1.90-1.20 (4H, m), 1.60-3.50 (1H, m), 1.43-1.37 (2H, m), 1.35 (3H, s), 1.16 (3H, s), 1.15-1.10 (1H, m).

LC-MS (condition 1); [M+H]$^+$ 443.9/Rt. (min.) 0.79

Example 2-17

Examples 2-17 shown in the following table were prepared from each corresponding starting compound in the manner of Reference example 16 and Example 1.

| Example | R$^{1A}$ | R$^{1B}$ | R$^{1C}$ | R$^{1D}$ | Q | Racemic or Chiral | Starting compound | LC-MS (Condition 1): [M + H]$^+$/ Rt (min) |
|---|---|---|---|---|---|---|---|---|
| 2 | H | H | F | H | 2-methylimidazol-1-yl (Me) | Racemic | Reference example 11 | 428.2/0.73 |
| 3 | H | H | Cl | H | 2-methylimidazol-1-yl (Me) | Chiral | Reference example 3 | 443.9/0.79 |
| 4 | H | H | Cl | H | 2-methylimidazol-1-yl (Me) | Chiral | Reference example 4 | 443.9/0.79 |
| 5 | H | Cl | H | H | 2-methylimidazol-1-yl (Me) | Racemic | Reference example 7 | 444.0/0.83 |
| 6 | Cl | H | H | H | 2-methylimidazol-1-yl (Me) | Racemic | Reference example 5 | 444.0/0.78 |

-continued

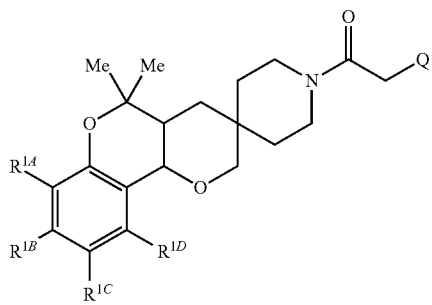

| Example | R$^{1A}$ | R$^{1B}$ | R$^{1C}$ | R$^{1D}$ | Q | Racemic or Chiral | Starting compound | LC-MS (Condition 1): [M + H]$^+$/ Rt (min) |
|---|---|---|---|---|---|---|---|---|
| 7 | H | H | Br | H | 2-Me-imidazol-1-yl | Racemic | Reference example 14 | 488.0/0.82 |
| 8 | R | Br | H | H | 2-Me-imidazol-1-yl | Racemic | Reference example 10 | 488.0/0.83 |
| 9 | Br | H | H | H | 2-Me-imidazol-1-yl | Racemic | Reference example 6 | 488.0/0.81 |
| 10 | H | H | Na | H | 2-Me-imidazol-1-yl | Racemic | Reference example 15 | 451.0/0.75 |
| 11 | H | H | Na | H | 2-CN-imidazol-1-yl | Racemic | Reference example 15 | 462.4/1.09 |
| 12 | H | H | Cl | H | 2-CN-imidazol-1-yl | Racemic | Reference example 2 | 455.3/1.12 |
| 13 | H | H | Cl | H | 4-(hydroxymethyl)imidazol-1-yl | Racemic | Reference example 2 | 460.6/0,75 |
| 14 | H | H | Cl | H | 5-Me-4-(hydroxymethyl)imidazol-1-yl | Racemic | Reference example 2 | 474.0/0.76 |

-continued

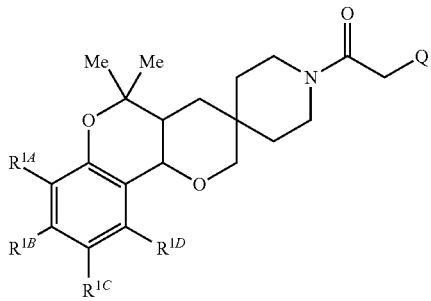

| Example | R^{1A} | R^{1B} | R^{1C} | R^{1D} | Q | Racemic or Chiral | Starting compound | LC-MS (Condition 1): [M + H]+/ Rt (min) |
|---|---|---|---|---|---|---|---|---|
| 15 | H | H | Cl | H | 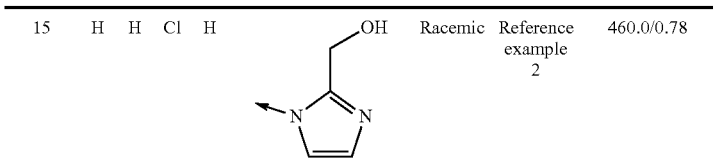 | Racemic | Reference example 2 | 460.0/0.78 |
| 16 | H | H | Cl | H | 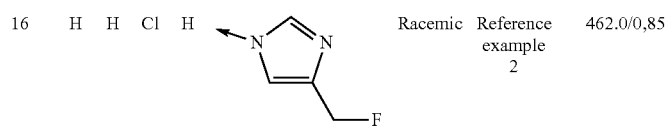 | Racemic | Reference example 2 | 462.0/0.85 |
| 17 | H | H | Cl | H | 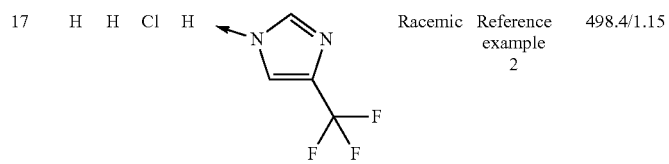 | Racemic | Reference example 2 | 498.4/1.15 |

The NMR data of Examples 2 and 7 shown in the above table are shown below.

Example 2

$^1$H-NMR (400 MHz, DMSO-d6): 7.08-6.95 (2H, m), 6.90-6.66 (1H, m), 6.79-6.69 (1H, m), 6.66 (1H, m), 4.89 (2H, m), 4.18 (1H, d, J=10.8 Hz), 4.00 (1H, d, J=12.0 Hz), 3.50-3.30 (5H, m), 2.12 (3H, s), 1.86-1.83 (1H, m), 1.74-1.66 (2H, m), 1.64-1.50 (1H, m), 1.40-1.33 (2H, m), 1.35-1.30 (1H, m), 1.33 (3H, s), 1.17-1.13 (1H, m), 1.13 (3H, s).

Example 7

$^1$H-NMR (400 MHz, DMSO-d6): 7.39 (1H, s), 7.30 (1H, d, J=8.4 Hz), 6.88 (1H, s), 6.72-6.66 (2H, m), 4.90-4.88 (2H, m), 4.19 (1H, d, J=10.8 Hz), 4.01 (1H, d, J=11.6 Hz), 3.50-3.36 (1H, m), 2.12 (3H, s), 1.86-1.83 (1H, m), 1.76-1.66 (2H, m), 1.64-1.53 (1H, m), 1.40-1.33 (2H, m), 1.36-1.31 (1H, m), 1.34 (3H, s), 1.18-1.1.3 (1H, m), 1.14 (3H, s).

Example 18

Racemate of (4'aR,10'bR)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran] and (4'aS,10'bS)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran]

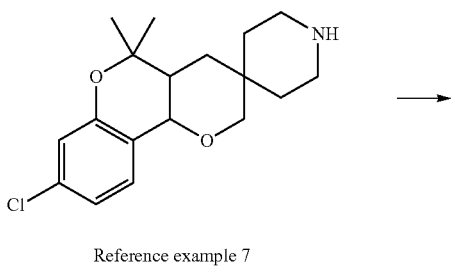

Reference example 7

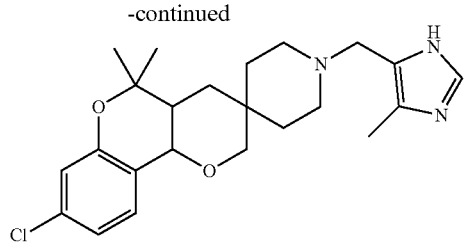

Example 18

To a solution of Reference example 7 (200 mg) in tetrahydrofuran (10 mL) were added 4-methyl-1H-imidazole-5-carbaldehyde (137 mg), and then sodium triacetoxyborohydride (397 mg) at 0° C., and the reaction mixture was stirred at 0° C. under a nitrogen atmosphere for 2 hours. To the reaction mixture were added water and saturated sodium carbonate, and the mixture was extracted with ethyl acetate. The organic layer was washed with saturated aqueous sodium carbonate and the brine, dried over magnesium sulfate, filtrated, and then concentrated in vacuo. The obtained residue was purified by silica gel column chromatography (chloroform/methanol) to give Example 18 (49 mg).

$^1$H-NMR (400 MHz, DMSO-d6): 11.61 (1H, d, J=17.7 Hz), 7.35 (1H, d, J=7.9 Hz), 7.28 (1H, d, J=7.9 Hz), 6.87 (1H, d, J=7.9 Hz), 6.77 (1H, s), 4.11 (1H, d, J=10.4 Hz), 3.87 (1H, d, J=10.4 Hz), 3.34-3.26 (3H, m), 2.49 (3H, s), 2.31-2.22 (4H, m), 2.11-2.03 (1H, m), 1.71-1.67 (2H, m), 1.60-1.56 (1H, m), 1.49-1.44 (1H, m), 1.31 (3H, s), 1.13 (3H, s), 1.13-1.08 (2H, m).

LC-MS (Condition 1); [M+H]$^+$ 416.7/Rt (min.) 0.59

Examples 19-37

Examples 19-37 shown in the following table were prepared from each corresponding starting compound in the manner of Example 18.

| Example | R$^{1A}$ | R$^{1B}$ | R$^{1C}$ | R$^{1D}$ | Q | Racemic or Chiral | Starting compound | LC-MS (Condition 1): [M + H]$^+$/Rt (min) |
|---|---|---|---|---|---|---|---|---|
| 19 | H | Cl | H | K | 4-Me-imidazole | Chiral | Reference example 8 | 416.3/0.60 |
| 20 | H | Cl | H | H | 4-Me-imidazole | Chiral | Reference example 9 | 416.3/0.59 |
| 21 | H | H | F | H | 4-Me-imidazole | Racemic | Reference example 11 | 400.4/0.61 |
| 22 | H | H | F | H | 4-Me-imidazole | Chiral | Reference example 12 | 400.3/0.60 |
| 23 | H | H | F | H | 4-Me-imidazole | Chiral | Reference example 13 | 400.3/0.61 |

-continued

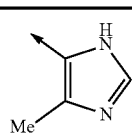

| Example | R$^{1A}$ | R$^{1B}$ | R$^{1C}$ | R$^{1D}$ | Q | Racemic or Chiral | Starting compound | LC-MS (Condition 1): [M + H]$^+$/Rt (min) |
|---|---|---|---|---|---|---|---|---|
| 24 | H | H | Cl | H | 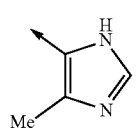 | Racemic | Reference example 2 | 416.0/0.60 |
| 25 | H | H | Cl | H | 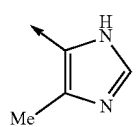 | Chiral | Reference example 3 | 416.0/0.61 |
| 26 | H | H | Cl | H | 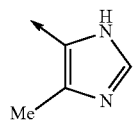 | Chiral | Reference example 4 | 416.1/0.60 |
| 27 | Cl | H | H | H | 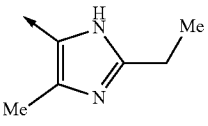 | Racemic | Reference example 5 | 416.4/0.66 |
| 28 | H | H | Cl | H | 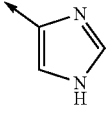 | Racemic | Reference example 2 | 444.3/0.66 |
| 29 | H | H | Cl | H | 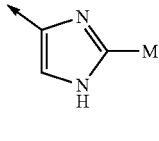 | Racemic | Reference example 2 | 402.3/0.75 |
| 30 | H | H | Cl | H | 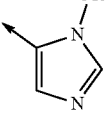 | Racemic | Reference example 2 | 416.3/0.70 |
| 31 | H | H | F | H | 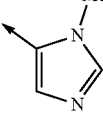 | Racemic | Reference example 11 | 400.4/0.55 |
| 32 | H | H | Cl | H | 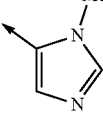 | Racemic | Reference example 2 | 416.6/0.57 |

-continued

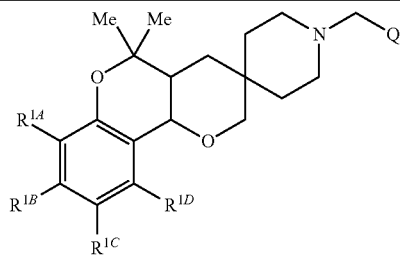

| Example | $R^{1A}$ | $R^{1B}$ | $R^{1C}$ | $R^{1D}$ | Q | Racemic or Chiral | Starting compound | LC-MS (Condition 1): [M + H]$^+$/Rt (min) |
|---|---|---|---|---|---|---|---|---|
| 33 | H | Cl | H | H | Me-N-imidazolyl | Racemic | Reference example 7 | 418.6/0.93 |
| 34 | Cl | H | H | H | Me-N-imidazolyl | Racemic | Reference example 5 | 416.3/0.62 |
| 35 | H | H | Cl | H | H-N-imidazolyl | Racemic | Reference example 2 | 402.0/0.70 |
| 36 | H | H | Cl | H | N-Me-imidazolyl | Racemic | Reference example 2 | 416.0/0.77 |
| 37 | H | Cl | H | H | Me-imidazolyl-CH=CH-CH₂-OH | Chiral | Reference example 9 | 486.4/0.65 |

The NMR data of Example 20 and 33 Shown in the above table are shown below.

Example 20

$^1$H-NMR (400 MHz, DMSO-d6): 11.61 (1H, d, J=17.7 Hz), 7.35 (1H, d, J=7.9 Hz), 7.28 (1H, d, J=0.9 Hz), 6.87 (1H, d, J=7.9 Hz), 6.77 (1H, s), 4.11 (1H, d, J=10.4 Hz), 3.87 (1H, d, J=10.4 Hz), 3.34-3.26 (3H, m), 2.49 (3H, s), 2.31-2.22 (4H, m), 2.11-2.03 (1H, m), 1.71-1.67 (21H, m), 1.60-1.56 (1H, m), 1.49-1.44 (1H, m), 1.31 (3H, s), 1.13 (0.3H, s), 1.13-1.08 (2H, m).

Example 33

$^1$H-NMR (400 MHz, DMSO-d6): 7.50 (1H, s), 7.29 (1H, d, J=7.6 Hz), 6.89 (1H, d, J=8.4 Hz), 6.77 (1H, s), 6.71 (1H, s), 4.12 (1H, d, J=10.8 Hz), 3.88 (1H, d, J=10.4 Hz), 3.58 (3H, m), 3.44-3.30 (2H, m), 2.39-2.20 (4H, m), 1.74-1.70 (2H, m), 1.60-1.51 (2H, m), 1.50-1.30 (2H, m), 1.32 (3H, s), 1.14 (3H, s), 1.13-1.10 (1H, m).

Example 38

Racemate of (4'aR,10'bR)-8'-chloro-1-[2-(1H-imidazol-1-yl)ethyl]-5',5'-dimethyl-4'a,10'b-dihydro-2'H, 4'H,5'H-spiro[piperidine-4,3'-pyrano[3,2-c][1]benzopyran] and (4'aS,10'bS)-8'-chloro-1-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran]

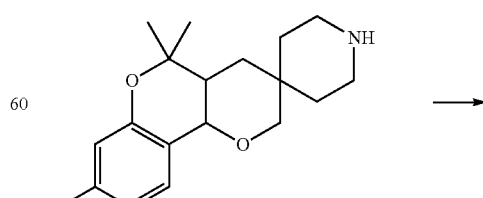

Reference example 7

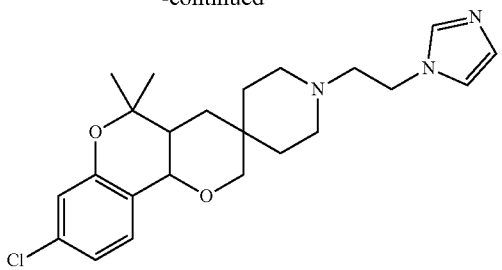

Example 38

To a solution of Reference example 7 (200 mg) in acetonitrile (10.0 mL) were added 2-bromoethanol (137 mg) and triethylamine (0.70 mL) at 0° C., and the reaction mixture was stirred at 70° C. under a nitrogen atmosphere for an hour. The reaction mixture was cooled to 0° C., and concentrated. Dichloromethane (10.0 mL), triethylamine (0.57 mL), and methanesulfonyl chloride (0.09 mL) were added thereto, and the reaction mixture was stirred for 30 minutes. Imidazole (0.50 g) was added thereto at room temperature, and the reaction mixture was stirred at 50° C. under a nitrogen atmosphere for an hour. To the reaction mixture were added saturated aqueous sodium carbonate, and the mixture was extracted with ethyl acetate. The organic layer was washed with saturated aqueous sodium carbonate and then brine, dried over magnesium sulfate, filtrated, and then concentrated in vacuo. The obtained residue was purified by silica gel column chromatography (chloroform/methanol) to give Example 38 (49 mg).

$^1$H-NMR (400 MHz, DMSO-d6): 7.59 (1H, s), 7.29 (1H, d, J=7.9 Hz), 7.15 (1H, s), 6.88 (1H, d, J=8.5 Hz), 6.83 (1H, s), 6.78 (1H, s), 4.12 (1H, d, J=11.2 Hz), 4.04-4.01 (2H, m), 3.90 (1H, d, J=10.8 Hz), 3.32-3.26 (3H, m), 2.59 (2H, t, J=6.0 Hz), 2.52-2.46 (4H, m), 2.43-2.25 (4H, m), 1.73 (2H, d, J=7.9 Hz), 1.60-1.56 (1H, m), 1.49-1.44 (1H, m), 1.32 (3H, s), 1.13 (3H, s), 1.13-1.08 (2H, m).

LC-MS (Condition 1); [M+H]$^+$ 416.7/Rt (min.) 0.59

Examples 39-63

Examples 39-63 shown in the following table were prepared from each corresponding starting compound in the manner of Example 38.

| Example | $R^{1A}$ | $R^{1B}$ | $R^{1C}$ | $R^{1D}$ | Q | Racemic or Chiral | Starting compound | LC-MS (Condition): [M + H]$^+$/Rt (min) |
|---|---|---|---|---|---|---|---|---|
| 35 | H | H | F | H | imidazol-1-yl-CH₂- | Racemic | Reference example 11 | 400.4/0,52 |
| 40 | H | H | Cl | H | imidazol-1-yl-CH₂- | Racemic | Reference example 2 | 416.3/0.57 |
| 41 | H | Cl | H | H | imidazol-1-yl-CH₂- | Chiral | Reference example 8 | 416,3/0.57 |
| 42 | H | Cl | H | H | imidazol-1-yl-CH₂- | Chiral | Reference example 9 | 416.3/0.58 |
| 43 | H | H | F | H | 2-Me-imidazol-1-yl-CH₂- | Racemic | Reference example 11 | 414.4/0.53 |
| 44 | H | H | F | H | 2-Me-imidazol-1-yl-CH₂- | Chiral | Reference example 12 | 414.4/0.54 |

-continued

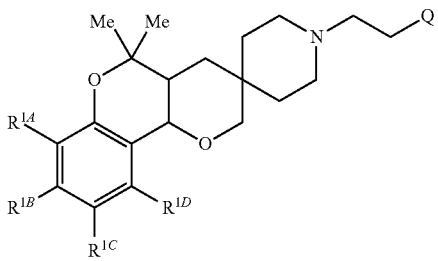

| Example | R^{1A} | R^{1B} | R^{1C} | R^{1D} | Q | Racemic or Chiral | Starting compound | LC-MS (Condition): [M + H]^+/Rt (min) |
|---|---|---|---|---|---|---|---|---|
| 45 | H | H | F | H | Me-imidazole | Chiral | Reference example 13 | 414.4/0.54 |
| 46 | H | H | Cl | H | Me-imidazole | Racemic | Reference example 2 | 430.3/0.57 |
| 47 | H | H | Cl | H | Me-imidazole | Chiral | Reference example 3 | 430.3/0.57 |
| 48 | H | H | Cl | H | Me-imidazole | Chiral | Reference example 4 | 430.4/0.58 |
| 49 | H | Cl | H | H | Me-imidazole | Racemic | Reference example 7 | 430.3/0.60 |
| 50 | H | Cl | H | H | Me-imidazole | Chiral | Reference example 8 | 430.3/0.63 |
| 51 | H | Cl | H | H | Me-imidazole | Chiral | Reference example 9 | 430.3/0.61 |
| 52 | H | H | F | H | OH-CH2-imidazole | Racemic | Reference example 11 | 430.4/0.55 |
| 53 | H | H | Cl | H | OH-CH2-imidazole | Racemic | Reference example 2 | 446.3/0.61 |

-continued
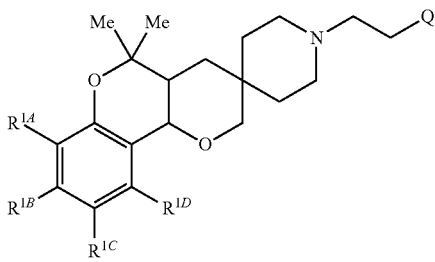
| Example | R$^{1A}$ | R$^{1B}$ | R$^{1C}$ | R$^{1D}$ | Q | Racemic or Chiral | Starting compound | LC-MS (Condition): [M + H]$^+$/Rt (min) |
|---|---|---|---|---|---|---|---|---|
| 54 | H | Cl | H | H | 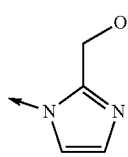 | Racemic | Reference example 7 | 446.3/0.61 |
| 55 | H | H | Cl | H | 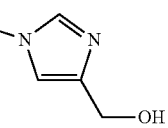 | Racemic | Reference example 2 | 446.3/0.61 |
| 56 | H | H | Cl | H | 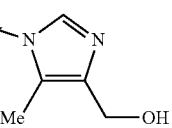 | | Reference example 2 | |
| 57 | H | Cl | H | H | 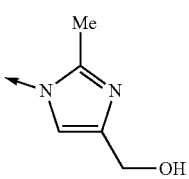 | Racemic | Reference example 7 | 460.3/0.62 |
| 58 | H | H | Cl | H | 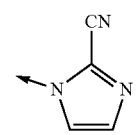 | Racemic | Reference example 2 | 441.0/0.84 |
| 59 | H | H | Cl | H | 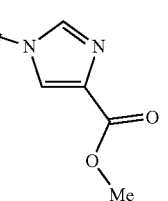 | Racemic | Reference example 2 | 474.3/1.15 |
| 60 | H | Cl | H | H | 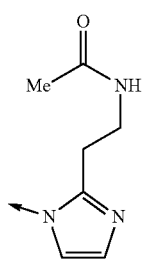 | Chiral | Reference example 9 | 501.2/0.76 |

-continued

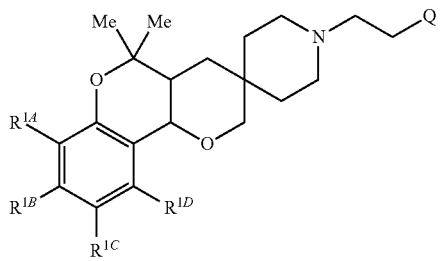

| Example | $R^{1A}$ | $R^{1B}$ | $R^{1C}$ | $R^{1D}$ | Q | Racemic or Chiral | Starting compound | LC-MS (Condition): $[M + H]^+$/Rt (min) |
|---|---|---|---|---|---|---|---|---|
| 61 | H | Cl | H | H | 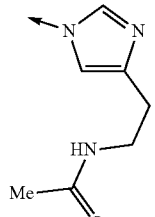 | Chiral | Reference example 9 | 501.3/0.66 |
| 62 | H | Cl | H | H | 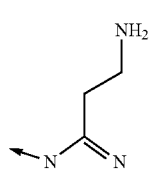 | Chiral | Reference example 9 | 459.2/0.89 |
| 63 | H | Cl | H | H | 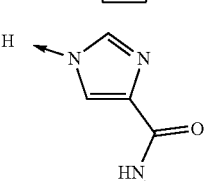 | Chiral | Reference example 9 | 473.3/0.74 |

The NMR data of Examples 42, 60, 61, and 63 shown in the above table are shown below.

Example 42

$^1$H-NMR (400 MHz, DMSO-d6): 7.59 (1H, s), 7.29 (1H, d, J=7.9 Hz), 7.15 (1H, s), 6.88 (1H, d, J=8.5 Hz), 6.83 (1H, s), 6.78 (1H, s), 4.12 (1H, d, J=11.2 Hz), 4.04-4.01 (2H, m), 3.90 (1H, d, J=10.8 Hz), 3.32-3.26 (3H, m), 2.59 (2H, t, J=6.0 Hz), 2.52-2.46 (4H, m), 2.43-2.25 (4H, m), 1.73 (2H, d, J=7.9 Hz), 1.60-1.56 (1H, m), 1.49-1.44 (1H, m), 1.32 (3H, s), 1.13 (3H, s), 1.13-1.08 (2H, m).

Example 60

$^1$H-NMR (400 MHz, CDCl$_3$): 7.34 (1H, d, J=8.0 Hz), 7.31 (1H, s), 6.99-6.90 (2H, m), 6.99 (1H, d, J=8.4 Hz), 6.82 (1H, s), 4.11-4.07 (2H, m), 4.00-3.96 (2H, m), 3.76-3.72 (2H, m), 3.33 (1H, d, J=11.2 Hz), 2.93-2.90 (2H, m), 2.67-2.66 (2H, m), 2.55-2.45 (3H, m), 2.39-2.32 (1H, m), 1.99 (3H, s), 1.91-1.87 (2H, m), 1.80-1.77 (1H, m), 1.65-1.55 (1H, m), 1.44-1.41 (2H, m), 1.41 (3H, s), 1.29 (3H, s), 1.21-1.12 (1H, m).

Example 61

$^1$H-NMR (400 MHz, CDCl$_3$): 7.42 (1H, s), 7.21 (1H, d, J=8.4 Hz), 7.18 (1H, s), 6.77 (1H, d, J=8.4 Hz), 6.69-6.67 (2H, m), 6.54 (1H, s), 3.99-3.96 (2H, m), 3.91-3.88 (2H, m), 3.43-3.42 (2H, m), 3.21 (1H, d, J=11.2 Hz), 2.67-2.64 (2H, m), 2.61-2.58 (2H, m), 2.45-2.35 (3H, m), 2.30-2.24 (1H, m), 1.87 (3H, s), 1.76-1.67 (2H, m), 1.53-1.49 (1H, m), 1.42-1.38 (1H, m), 1.35-1.30 (1H, m), 1.28 (3H, s), 1.08 (3H, s), 1.04-0.97 (1H, m).

Example 63

$^1$H-NMR (400 MHz, DMSO-d6): 8.18 (1H, d, J=4.4 Hz), 7.72 (1H, s), 7.45 (1H, s), 7.29 (1H, d, J=7.6 Hz), 6.88 (1H, d, J=7.6 Hz), 6.77 (1H, s), 4.37-4.33 (2H, m), 4.10 (1H, d, J=11.6 Hz), 3.88 (1H, d, J=11.6 Hz), 3.31-3.26 (2H, m), 2.70 (3H, s), 2.57-2.53 (2H, m), 2.37-2.29 (4H, m), 1.72-1.67 (2H, m), 1.60-1.55 (1H, m), 1.50-1.40 (1H, m), 1.32-1.23 (2H, m), 1.29 (3H, s), 1.13 (3H, s), 1.13-1.06 (1H, m).

Example 64

Racemate of (4'aS,10'bR)-8'-chloro-1-[(4-methyl-1H-imidazol-5-yl)methyl]-4'a,10'b-dihydro-2'H,4'H,5'H-spiro[piperidine-4,3'-pyrano[3,2-c][1]benzopyran] and (4'aR,10'bS)-8'-chloro-1-[(4-methyl-1H-imidazol-5-yl)methyl]-4'a,10'b-dihydro-2'H,4'H,5'H-spiro[piperidine-4,3'-pyrano[3,2-c][1]benzopyran]

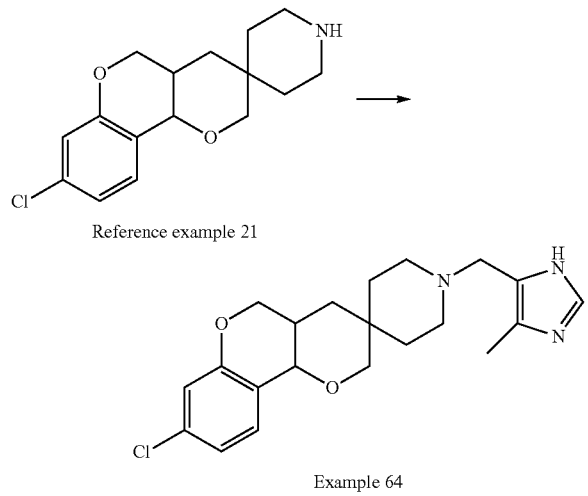

Reference example 21

Example 64

To a solution, of Reference example 21 (103 mg) and 4-methyl-1H-imidazole-5-carbaldehyde (77 mg) in THF (3.5 mL) and methanol (1.0 mL) was added sodium triacetoxyborohydride (223 mg), and the reaction mixture was stirred at room temperature for 2 hours. Additional sodium triacetoxyborohydride (77 mg) was added thereto, and the reaction mixture was stirred for additional 30 minutes. The reaction solution was concentrated and the obtained residue was purified by silica gel column chromatography (ethyl acetate/methanol) to give Example 64 (97 mg).

$^1$H-NMR (400 MHz, DMSO-d6): 11.65 (0.5H, s), 11.60 (0.5H, s), 7.35 (1H, s), 7.25 (1H, d, J=8.3 Hz), 6.89 (18, dd, J=8.3, 1.8 Hz), 6.81 (1H, d, J=1.8 Hz), 4.17 (1H, dd, J=11.0, 3.7 Hz), 4.12 (1H, d, J=10.4 Hz), 3.86-3.92 (2H, m), 3.26-3.38 (3H, m), 2.21-2.37 (4H, m), 2.11 (1.54, s), 2.03 (1.5H, s), 1.86-1.95 (1H, m), 1.75 (1H, d, J=12.2 Hz), 1.55 (2H, br), 1.27 (2H, br), 0.95 (1H, t, J=12.5 Hz), LC-MS (Condition 1); [M+H]$^+$ 388.7/Rt (min.) 0.57

Examples 64a and 64b

The obtained Example 64 was optically resolved to obtain Example 64a and Example 64b which are optical active compounds of Example 64.

Example 64a

Condition D; Rt (min.) 10.26

LC-MS (Condition 1); [M+H]$^+$ 388.1/Rt (min.) 0.60

Example 64b

Condition D; Rt (min.)=14.02

LC-MS (Condition 1); [M+H]$^+$ 388.0/Rt (min.) 0.61

Example 65

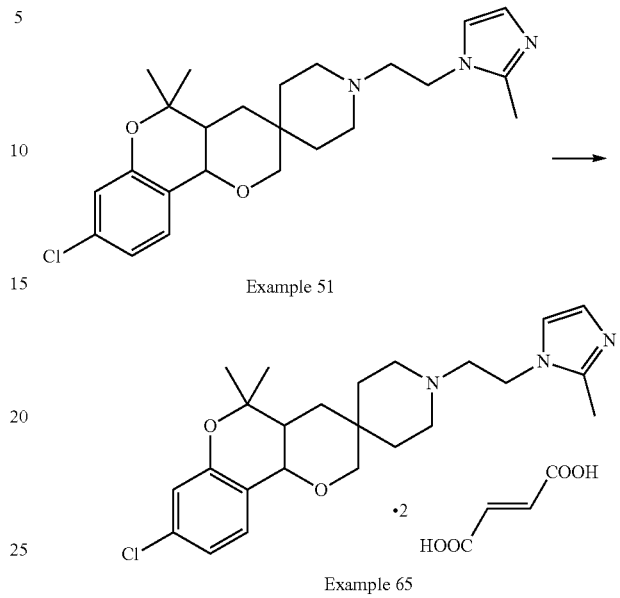

Example 51

Example 65

To a solution of Example 51 (15 mg) in methanol (0.2 mL) was added fumaric acid (8.1 mg), and the reaction mixture was stirred at 60° C. for an hour. The reaction mixture was left to stand at room temperature overnight, and dried up by vaporization. To the residue was added ethyl acetate (0.3 mL), and the mixture was stirred at 40° C. for 4 hours. The precipitated solid was collected on Kiriyama filter, washed with ethyl acetate, and dried at 50° C. in vacuo to give Example 65 (15 mg) as a white solid.

$^1$H-NMR (400 MHz, DMSO-d6) δ: 7.29 (1H, d, J=8.5 Hz), 7.11 (1H, d, J=1.2 Hz), 6.88 (1H, dd, J=8.2, 2.1 Hz), 6.81 (1H, d, J=1.2 Hz), 6.78 (1H, d, J=2.4 Hz), 6.59 (4H, s), 4.12 (1H, d, J=11.0 Hz), 3.97 (2H, t, =6.7 Hz), 3.90 (1H, d, J=11.6 Hz), 3.30 (1H, d, J=11.6 Hz), 2.59 (2H, t, J=6.4 Hz), 2.46-2.39 (2H, m), 2.38-2.25 (2H, m), 2.32 (3H, s), 1.81-1.65 (2H, m), 1.65-1.55 (1H, m), 1.37-1.23 (1H, m), 1.32 (3H, s), 1.15-1.05 (1H, m), 1.13 (3H, s).

LC-MS (Condition 2); [M+H]$^+$ 430/Rt. (min.) 1.519

Examples 66-78

Examples 66-78 shown in the following table were prepared from each corresponding starting compound by each salification like the manner of Example 65.

| Example | Salt | Valence | Starting compound | $^1$H-NMR (400 MHz, DMSO-d6) δ: |
|---|---|---|---|---|
| 66 | phosphate | 2 | Example 20 | 7.66 (1H, s), 7.29 (1H, d, J = 8.2 Hz), 6.89 (1H, dd, J = 8.2, 2.3 Hz), 6.79 (1H, d, J = 2.3 Hz), 5.70 (9H, brs), 4.15 (1H, d, J = 11.0 Hz), 3.94 (3H, s), 3.36 (1H, d, J = 11.4 Hz), 3.01-2.77 (4H, m), 2.19 (3H, s), 1.84-1.62 (4H, m), 1.54-1.47 (2H, m), 1.34 (3H, s), 1.14 (3H, s). |

| Example | Salt | Valence | Starting compound | ¹H-NMR (400 MHz, DMSO-d6) δ: |
|---|---|---|---|---|
| 67 | phosphate | 2 | Example 32 | 7.73 (1H, s), 7.24 (1H, dd, J = 2.7, 0.9 Hz), 7.16 (1H, dd, J = 8.7, 2.7 Hz), 6.92 (1H, s), 6.74 (1H, d, J = 8.7 Hz), 5.58 (10H, brs), 4.15 (1H, d, J = 11.0 Hz), 3.91 (1H, d, J = 11.0 Hz), 3.67 (2H, s), 3.63 (3H, s), 3.33 (1H, d, J = 11.4 Hz), 2.59-2.52 (2H, m), 1.83-1.52 (5H, m), 1.41-1.35 (2H, m), 1.33 (3H, s), 1.14-1.10 (1H, m). |
| 68 | fumarate | 2 | Example 34 | 7.56 (1H, s), 7.29 (1H, d, J = 4.6 Hz), 6.88 (1H, dd, J = 8.2, 2.3 Hz), 6.78 (1H, d, J = 1.8 Hz), 6.76 (1H, s), 6.60 (4H, s), 4.12 (1H, d, J = 10.5 Hz), 3.88 (1H, d, J = 11.4 Hz), 3.59 (3H, s), 3.47 (2H, s), 3.31 (1H, d, J = 11.4 Hz), 2.44-2.34 (3H, m), 2.33-2.24 (1H, m), 1.80-1.66 (2H, m), 1.65-1.45 (2H, m), 1.35-1.28 (2H, m), 1.32 (3H, s), 1.15-1.06 (1H, m), 1.13 (3H, s). |
| 69 | phosphate | 2 | Example 34 | 7.71 (1H, s), 7.29 (1H, d, J = 8.2 Hz), 6.90 (1H, s), 6.89 (1H, dd, J = 8.5, 2.1 Hz), 6.78 (1H, d, J = 1.8 Hz), 5.23 (13H, brs), 4.13 (d, 1H, J = 10.5 Hz), 3.90 (1H, d, J = 11.0 Hz), 3.65 (2H, s), 3.63 (3H, s), 3.33 (1H, d, J = 11.4 Hz), 2.60-2.48 (3H, m), 1.84-1.50 (4H, m), 1.40-1.35 (2H, m), 1.33 (3H, s), 1.15-10.8 (1H, m), 1.13 (3H, s). |
| 70 | p-toluene-sulfonate | 2 | Example 34 | 9.62-9.14 (0.5H, brm), 9.05 (1H, s), 7.79 (1H, s), 7.47 (4H, dt, J = 7.9, 2.1 Hz), 7.29 (1H, d, J = 8.5 Hz), 7.11 (4H, d, J = 7.9 Hz), 6.91 (1H, dd, J = 8.2, 2.1 Hz), 6.80 (1H, d, J = 1.8 Hz), 4.49 (1.5H, brs), 4.34 (0.5H, brs), 4.17 (1H, d, J = 10.4 Hz), 3.87 (3H, s), 3.63-2.94 (2H, m), 2.28 (6H, s), 1.79-1.69 (1H, m), 1.67-1.22 (6H, m), 1.15 (3H, s). |
| 71 | fumarate | 2 | Example 42 | 7.66 (1H, s), 7.29 (1H, d, J = 8.7 Hz), 7.18 (1H, s), 6.91-6.82 (2H, m), 6.78 (1H, d, J = 1.8 Hz), 6.61 (4H, s), 4.15-3.99 (3H, m), 3.90 (1H, d, J = 11.0 Hz), 3.30 (1H, d, J = 11.4 Hz), 2.65 (2H, t, J = 6.4 Hz), 2.47-2.29 (2H, m), 1.80-1.56 (3H, m), 1.56-1.44 (1H, m), 1.35-1.29 (2H, m), 1.32 (3H, s), 1.19-1.05 (1H, m), 1.13 (3H, s). |
| 72 | phosphate | 2 | Example 42 | 7.74 (1H, s), 7.29 (1H, d, J = 7.9 Hz), 7.21 (1H, s), 6.92 (1H, s), 6.89 (1H, dd, J = 8.2, 1.8 Hz), 6.78 (1H, d, J = 1.8 Hz), 4.15-4.07 (3H, m), 3.90 (1H, d, J = 11.0 Hz), 3.31 (1H, d, J = 11.0 Hz), 2.72 (2H, t, J = 6.0 Hz), 2.45-2.36 (2H, m), 1.81-1.58 (3H, m), 1.58-1.47 (1H, m), 1.38-1.27 (2H, m), 1.33 (3H, s), 1.17-1.06 (1H, m), 1.13 (3H, s). |
| 73 | p-toluene-sulfonate | 2 | Example 42 | 9.11 (1H, s), 7.78 (1H, t, J = 1.6), 7.72 (1H, t, J = 1.6 Hz), 7.47 (4H, dt, J = 8.2, 1.8 Hz), 7.30 (1H, d, J = 8.2 Hz), 7.11 (4H, d, J = 8.2 Hz), 6.91 (1H, dd, J = 8.2, 2.3 Hz), 6.80 (1H, d, J = 2.3 Hz), 4.62 (2H, t, J = 6.2 Hz), 4.17 (1H, d, J = 11.0 Hz), 3.65 (2H, brs), 3.28-2.89 (3H, m), 2.28 (6H, s), 2.23-2.00 (1H, m), 1.80-1.68 (1H, m), 1.68-1.43 (3H, m), 1.42-1.26 (4H, m), 1.15 (3H, s). |
| 74 | fumarate | 2 | Example 44 | 7.10 (1H, d, J = 1.4 Hz), 7.01 (1H, dd, J = 9.1, 3.2 Hz), 6.97 (1H, td, J = 8.5, 3.2 Hz), 6.80 (1H, d, J = 1.4 Hz), 6.72 (1H, dd, J - 8.9, 4.8 Hz), 6.59 (4H, s), 4.13 (1H, d, J = 10.5 Hz), 3.97 (2H, t, J = 6.4 Hz), 3.91 (1H, d, J = 11.4 Hz), 3.30 (1H, d, J = 11.4 Hz), 2.59 (2H, t, J = 6.6 Hz), 2.46-2.38 (3H, m), 2.38-2.31 (2H, m), 2.31 (3H, s), 1.79-1.56 (3H, m), 1.55-1.44 (1H, m), 1.36-1.26 (2H, m), 1.31 (3H, s), 1.14-1.05 (1H, m), 1.11 (3H, s). |
| 75 | phosphate | 2 | Example 44 | 7.27 (1H, d, J = 1.8 Hz), 7.04-6.98 (2H, m), 6.96 (1H, dd, J = 8.7, 3.2 Hz), 6.72 (1H, dd, J = 8.7, 4.6 Hz), 6.09 (10H, brs), 4.13 (1H, d, J = 11.0 Hz), 4.07 (2H, t, J = 6.4 Hz), 3.91 (1H, d, J = 11.4 Hz), 3.31 (1H, d, J = 11.4 Hz), 2.68 (2H, t, J = 6.4 Hz), 2.45-2.39 (2H, m), 2.40 (3H, s), 1.80-1.58 (3H, m), 1.57-1.46 (1H, m), 1.37-1.30 (2H, m), 1.31 (3H, s), 1.14-1.07 (1H, m), 1.11 (3H, s). |
| 76 | p-toluene-sulfonate | 2 | Example 44 | 9.41-9.16 (1H, brm), 7.66 (1H, d, J = 1.8 Hz), 7.61 (1H, d, J = 2.3 Hz), 7.47 (4H, dt, J = 8.2, 1.8 Hz), 7.11 (4H, dt, J = 7.8 Hz), 7.06-6.96 (2H, m), 6.74 (1H, dd, J = 8.9, 4.8 Hz), 4.50 (2H, t, J = 6.9 Hz), 4.38-4.12 (2H, m), 3.69-3.51 (3H, m), 3.28-2.98 (3H, m), 2.61 (3H, s), 2.28 (6H, s), 1.90 (1.5H, s), 1.80-1.59 (2H, m), 1.69-1.46 (2H, m), 1.40-1.27 (5H, m), 1.18-1.08 (4H, m). |
| 77 | phosphate | 2 | Example 51 | 7.29 (1H, d, J = 8.5 Hz), 7.22 (1H, d, J = 1.2 Hz), 6.95 (1H, d, J = 1.2 Hz), 6.88 (1H, dd, J = 8.2, 2.1 Hz), 6.78 (1H, d, J = 1.8 Hz), 5.47 (10H, brs), 4.12 (1H, d, J = 11.0 Hz), 4.01 (2H, t, J = 6.4 Hz), 3.90 (1H, d, J = 11.0 Hz), 3.31 (1H, d, J = 11.0 Hz), 2.64 (2H, t, J = 6.4 Hz), 2.48-2.42 (2H, m), 2.42-2.33 (2H, m), 2.37 (3H, s), 1.80-1.67 (2H, m), 1.66-1.56 (1H, m), 1,56-1.45 (1H, m), 1.38-1.27 (2H, m), 1.33 (3H, s), 1.15-1.07 (1H, m), 1.13 (3H, s). |
| 78 | p-toluene-sulfonate | 2 | Example 51 | 9.39-9.16 (1H, brm), 7.65 (1H, d, J = 1.8 Hz), 7.61 (1H, d, J = 1.8 Hz), 7.47 (4H, dt, J = 8.2, 1.8 Hz), 7.33-7.27 (1H, m), 7.11 (4H, dt, J = 7.8 Hz), 6.91 (1H, dd, J = 8.2, 2.3 Hz), 6.80 (1H, d, J = 2.3 Hz), 4.50 (2H, t, J = 6.9 Hz), 4.37-4.12 (2H, m), 3.68-3.51 (3H, m), |

-continued

| Example | Salt | Valence | Starting compound | $^1$H-NMR (400 MHz, DMSO-d6) δ: |
|---|---|---|---|---|
| | | | | 3.28-2.98 (3H, m), 2.61 (3H, s), 2.28 (6H, s), 2.25-2.07 (2H, m), 1.90 (1.5H, s), 1.80-1.47 (5H, m), 1.45-1.27 (5H, m), 1.21-1.08 (4H, m). |

Tests

Hereinafter, results that the compounds of the present invention were evaluated with pharmacological experiments are shown, which also explained about the pharmacological activity of the compounds, however, the technical scope of the present invention should not be limited thereto.

Test 1: Inhibition Test for Sphere Formation Assay of Cancer Cells

Reliable methods established for measuring the self-renewal ability of cells which is one of the CSC's properties include a method for measuring the sphere-forming ability of cancer cells in non-adherent condition in the absence of serum (Cancer Res 65, 5506-5511 (2005)). HT-29 cells were available from American Type Culture Collection (ATCC). HT-29 cells were cultured at 3'7° C. under 5% $CO_2$ using the McCoy's 5a medium containing 10% fetal bovine serum (FBS) and 1% penicillin/streptomycin. HT-29 cells were seeded in a 384 Well Black Clear Bottom Ultra-Low Attachment Microplate (Corning Cat. No. 3827) in an amount of 350-800 cells/well using the DMEM/F12 medium containing 2% B27 supplement (GIBCO), 20 ng/mL epidermal growth factor (EGF) (peprotech), 10 ng/mL basic fibroblast growth factor (bFGF) (peprotech), 5 μg/mL insulin (Sigma), and 1% penicillin/streptomycin. Each test compound was added into each well to adjust the final concentration of DMSO to 0.1%, and the cells were cultured for 4 days. The number of viable cells in each well was then measured with CellTiter-Glo™ Luminescent Cell Viability Assay (Promega) to calculate the concentration of each test compound for 50% inhibition of cell proliferation (Sphere $IC_{50}$ value; μmol/L).

The experiment of Test 1 was performed for each compound of each Example. The concentration of each test compound for 50% inhibition of cell proliferation (Sphere $IC_{50}$ value; μmol/L) is shown in the following Table.

| Example | $IC_{50}$ (μmol/L) |
|---|---|
| 1 | 0.08 |
| 2 | 0.24 |
| 3 | 0.08 |
| 4 | 0.31 |
| 5 | 0.41 |
| 6 | 0.61 |
| 7 | 0.09 |
| 8 | 0.31 |
| 9 | 0.77 |
| 10 | 0.24 |
| 11 | 4.09 |
| 12 | 0.55 |
| 13 | 1.20 |
| 14 | 0.40 |
| 15 | 0.30 |
| 16 | 4.40 |
| 17 | 8.30 |
| 18 | 0.02 |
| 19 | 0.04 |
| 20 | <0.01 |

-continued

| Example | $IC_{50}$ (μmol/L) |
|---|---|
| 21 | 0.21 |
| 22 | 0.24 |
| 23 | 0.06 |
| 24 | 0.09 |
| 25 | 0.07 |
| 26 | <0.01 |
| 27 | 0.35 |
| 28 | 0.09 |
| 29 | 0.81 |
| 30 | 2.28 |
| 31 | 0.06 |
| 32 | <0.01 |
| 33 | <0.01 |
| 34 | <0.01 |
| 35 | 0.21 |
| 36 | 0.04 |
| 37 | 0.25 |
| 38 | <0.01 |
| 39 | <0.01 |
| 40 | <0.01 |
| 41 | <0.01 |
| 42 | <0.01 |
| 43 | 0.05 |
| 44 | <0.01 |
| 45 | <0.01 |
| 46 | <0.01 |
| 47 | <0.01 |
| 48 | <0.01 |
| 49 | <0.01 |
| 50 | 0.03 |
| 51 | <0.01 |
| 52 | <0.01 |
| 53 | <0.01 |
| 54 | <0.01 |
| 55 | 0.06 |
| 56 | <0.01 |
| 57 | 0.07 |
| 58 | 0.07 |
| 59 | 0.98 |
| 60 | 0.16 |
| 61 | 1.30 |
| 62 | N.D. |
| 63 | 6.8 |
| 64 | 0.07 |
| 64a | <0.01 |
| 64b | 0.05 |

As shown in the above table, Examples 20, 26, 32, 33, 34, 38, 39, 40, 41, 42, 44, 45, 46, 47, 48, 49, 51, 52, 53, 54, 56, and 64a exhibited potent activity for inhibiting cell proliferation in the sphere culture condition.

Test 2: Test for Evaluating hERG Inhibition

To a cultured CHO cell strain which stably expresses hERG was added each test compound to adjust the final concentration of DMSO to 0.0135 to 0.5%. The hERG current was measured with QPatch HT (Sophion Inc.), and the concentration at which 50% of the hERG current was inhibited by each test compound ($IC_{50}$ value; μM) was calculated.

The compounds of Examples were tested according to Test 2. And, the hERG/HT-29 was calculated by dividing the compound con-centration obtained in Test 2 (50% of the hERG current is inhibited) by the compound concentration obtained in Test 1 (50% of the proliferation of HT-29 cells is inhibited). The results are shown in the following table.

| Example | Binding inhibition ($IC_{50}$, μM) | hERG/HT-29 |
|---|---|---|
| 1 | <0.3 | — |
| 2 | <0.3 | — |
| 3 | 0.2 | 2.50 |
| 4 | <0.3 | — |
| 5 | <0.3 | — |
| 6 | <0.3 | — |
| 7 | <0.3 | — |
| 8 | 0.3 | 0.97 |
| 9 | <0.3 | — |
| 10 | <0.3 | — |
| 11 | 4.9 | 1.20 |
| 12 | 2.9 | 5.27 |
| 13 | 1.3 | 1.08 |
| 14 | 0.3 | 0.75 |
| 15 | 1.6 | 5.33 |
| 16 | 1.9 | 0.43 |
| 17 | 3.0 | 0.36 |
| 18 | 0.6 | 30 |
| 19 | 0.4 | 10 |
| 20 | 1.4 | >140 |
| 21 | 1.5 | 7.14 |
| 22 | 1.6 | 6.67 |
| 23 | 1.4 | 23.3 |
| 24 | 3.8 | 42.2 |
| 25 | 0.4 | 5.7 |
| 26 | 0.6 | >60 |
| 27 | 0.4 | 1.14 |
| 28 | 0.7 | 7.78 |
| 29 | 2.6 | 3.21 |
| 30 | 1.7 | 7.46 |
| 31 | 1.4 | 23.3 |
| 32 | 0.8 | >80 |
| 33 | 1.4 | >140 |
| 34 | 1.4 | >140 |
| 35 | 3.5 | 16.7 |
| 36 | 1.0 | 25.0 |
| 37 | N.D. | — |
| 38 | 0.8 | >80 |
| 39 | 1.0 | >100 |
| 40 | 1.4 | >140 |
| 41 | 0.7 | >70 |
| 42 | 1.4 | >140 |
| 43 | 1.0 | 20 |
| 44 | 3.6 | >360 |
| 45 | 0.4 | >40 |
| 46 | 1.2 | >120 |
| 47 | 1.9 | >190 |
| 48 | 0.8 | >80 |
| 49 | 1.4 | >140 |
| 50 | 1.5 | 50 |
| 51 | 0.9 | >90 |
| 52 | 1.5 | >150 |
| 53 | 0.8 | >80 |
| 54 | 1.4 | >140 |
| 55 | 1.6 | 26.7 |
| 56 | 0.8 | >80 |
| 57 | 1.1 | 15.7 |
| 58 | 1.9 | 27.1 |
| 59 | 0.4 | 0.41 |
| 60 | 1.1 | 6.88 |
| 61 | N.D. | — |
| 62 | 6.3 | — |
| 63 | N.D. | — |
| 64 | 0.4 | 5.71 |
| 64a | 0.6 | >60 |
| 64b | <0.3 | — |

As shown in the above table, Examples 20, 26, 32, 33, 34, 38, 39, 40, 41, 42, 44, 46, 47, 48, 49, 51, 52, 53, 54, 56, and 64a exhibited good deviation between the concentration of inhibiting 50% cell proliferation and the concentration of inhibiting 50% hERG current.

INDUSTRIAL APPLICABILITY

The compounds of the present invention have a potent inhibitory effect on the sphere-forming ability of cancer cells and thereby are useful as an anti-tumor agent.

The invention claimed is:

1. A process for preparing a compound of Formula (1a):

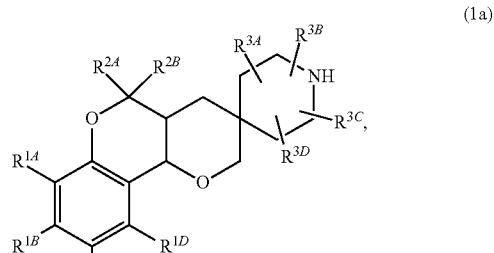

(1a)

or a pharmaceutically acceptable salt thereof, wherein:
  $R^{1A}$, $R^{1B}$, $R^{1C}$, and $R^{1D}$ are each independently hydrogen atom, halogen atom, azide, or cyano, provided that all of $R^{1A}$, $R^{1B}$, $R^{1C}$, and $R^{1D}$ are not hydrogen atom;
  $R^{2A}$ and $R^{2B}$ are each independently hydrogen atom or $C_{1-6}$ alkyl;
  $R^{3A}$, $R^{3B}$, $R^{3C}$, and $R^{3D}$ are each independently hydrogen atom, halogen atom, hydroxy, $C_{1-6}$ alkyl, $C_{1-6}$ alkoxy, —$CO_2R^4$, —$NR^5R^6$, or —$NR^7COR^8$, or any two of $R^{3A}$, $R^{3B}$, $R^{3C}$, and $R^{3D}$ may be taken together at the common carbon atom to which they are attached to form =O;
  $R^4$ and $R^8$ are each independently $C_{1-3}$ alkyl, and $R^5$, $R^6$, and $R^7$ are each independently hydrogen atom or $C_{1-3}$ alkyl, or when $R^5$ and $R^6$ are both $C_{1-3}$ alkyl, they may be combined with the nitrogen atom to which they are attached to form 3- to 6-membered nitrogen-containing saturated heterocyclyl, comprising the following steps:

A1) reacting a compound of Formula (7a):

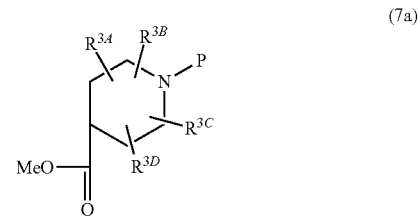

(7a)

wherein:
  P is an amino-protecting group; and
  $R^{3A}$, $R^{3B}$, $R^{3C}$, and $R^{3D}$ are as defined above;
with a compound of Formula (7b):

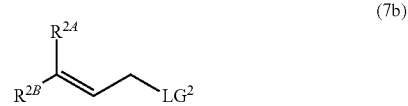

(7b)

wherein:
LG$^2$ is a leaving group; and
R$^{2A}$ and R$^{2B}$ are as defined above;
to give a compound of Formula (7c):

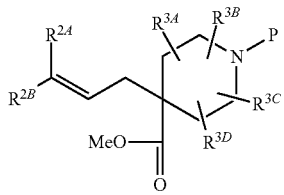

(7c)

wherein P, R$^{2A}$, R$^{2B}$, R$^{3A}$, R$^{3B}$, R$^C$, and R$^{3D}$ are as defined above;

A2) reducing the compound of Formula (7c) above, to give the compound of Formula (6b):

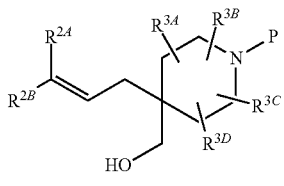

(6b)

wherein P, R$^{2A}$, R$^{2B}$, R$^{3A}$, R$^{3B}$, R$^{3C}$, and R$^{3D}$ are as defined above;

A3) reacting the compound of Formula (6b) above with a compound of Formula (6a):

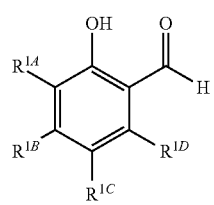

(6a)

wherein R$^{1A}$, R$^{1B}$, R$^{1C}$, and R$^{1D}$ are as defined above;
to give the compound of Formula (6b):

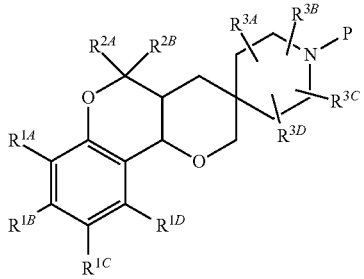

(6c)

wherein P, R$^{1A}$, R$^{1B}$, R$^{1C}$, R$^{1D}$, R$^{2A}$, R$^{2B}$, R$^{3A}$, R$^{3B}$, R$^{3C}$, and R$^{3D}$ are as defined above; and A4) deprotecting the compound of Formula (6c) above, to give the compound of Formula (1a) above.

2. A process for preparing a compound of Formula (5c):

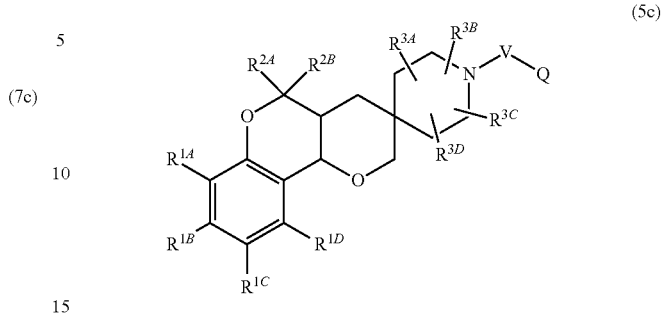

(5c)

or a pharmaceutically acceptable salt thereof,
wherein:
V is C$_{1-6}$ alkylene which may be substituted with 1 to 3 substituents selected independently from the group consisting of fluorine atom, hydroxy, C$_{1-6}$ alkoxy, C$_{3-7}$ cycloalkyl, 3- to 7-membered saturated heterocyclyl, cyano, and azide;
Q is optionally-substituted imidazole group;
R$^{1A}$, R$^{1B}$, R$^{1C}$, and R$^{1D}$ are each independently hydrogen atom, halogen atom, azide, or cyano, provided that all of R$^{1A}$, R$^{1B}$, R$^{1C}$, and R$^{1D}$ are not hydrogen atom;
R$^{2A}$ and R$^{2B}$ are each independently hydrogen atom or C$_{1-6}$ alkyl;
R$^{3A}$, R$^{3B}$, R$^{3C}$, and R$^{3D}$ are each independently hydrogen atom, halogen atom, hydroxy, C$_{1-6}$ alkyl, C$_{1-6}$ alkoxy, —CO$_2$R$^6$, —NR$^5$R$^6$, or —NR$^7$COR$^8$, or any two of R$^{3A}$, R$^{3B}$, R$^{3C}$, and R$^{3D}$ may be taken together at the common carbon atom to which they are attached to form =O;
R$^4$ and R$^8$ are each independently C$_{1-3}$ alkyl, and
R$^5$, R$^6$, and R$^7$ are each independently hydrogen atom or C$_{1-3}$ alkyl, or when R$^5$ and R$^6$ are both C$_{1-3}$ alkyl, they may be combined with the nitrogen atom to which they are attached to form 3- to 6-membered nitrogen-containing saturated heterocyclyl,
comprising the following steps:
B1) reacting a compound of Formula (1a):

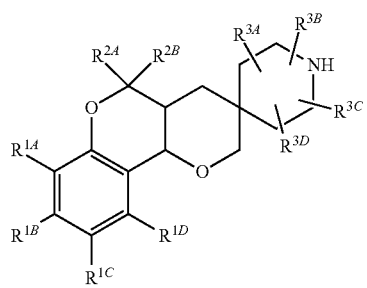

(1a)

or a pharmaceutically acceptable salt thereof,
wherein R$^{1A}$, R$^{1B}$, R$^{1C}$, R$^{1D}$, R$^{2A}$, R$^{2B}$, R$^{3A}$, R$^{3B}$, R$^{3C}$, and R$^{3D}$ are as defined above;
with a compound of Formula (5a):

(5a)

wherein:
LG² denotes a leaving group; and
V is as defined above;
to give a compound of Formula (5b):

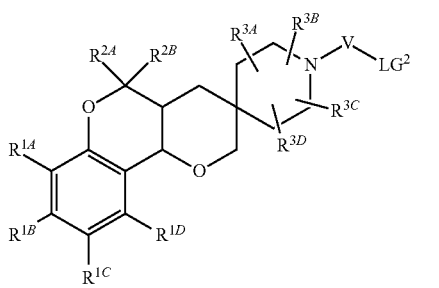

(5b)

wherein LG², V, $R^{1A}$, $R^{1B}$, $R^{1C}$, $R^{1D}$, $R^{2A}$, $R^{2B}$, $R^{3A}$, $R^{3B}$, $R^{3C}$, and $R^{3D}$ are as defined above; and B2) reacting the compound of Formula (5b) above with an imidazole derivate (QH) to give the compound of Formula (5c) above.

3. The method of claim 2 wherein the compound of Formula (5c) or a pharmaceutically acceptable salt thereof is at least one selected from the group consisting of:
(4'aS,10'bS)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran];
(4'aR,10'bR)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran];
(4'aR,10'bR)-8'-chloro-1-(2-(1H-imidazol-1-yl)ethyl)-5',5'-dimethyl-4'a,10'b-dihydro-2'H,4'H,5'H-spiro[piperidine-4,3'-pyrano[3,2-c][1]benzopyran];
(4'aS,10'bS)-8'-chloro-1-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran];
(4'aS,10'bS)-9'-fluoro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran]; and
(4'aR,10'bR)-9'-fluoro-5',5'-dimethyl-1-[2-(2-methyl-1H-imidazol-1-yl)ethyl]-4'a,10'b-dihydro-2'H,4'H,5'H-spiro[piperidine-4,3'-pyrano[3,2-c][1]benzopyran].

4. A process for preparing a compound of Formula (4b):

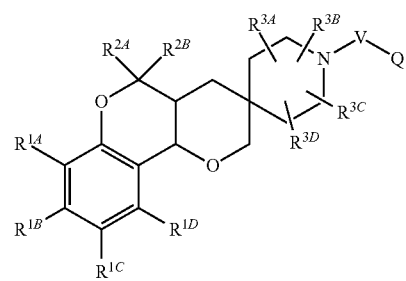

(4b)

or a pharmaceutically acceptable salt thereof, wherein:
V is $C_{1-6}$ alkylene which may be substituted with 1 to 3 substituents selected independently from the group consisting of fluorine atom, hydroxy, $C_{1-6}$ alkoxy, $C_{3-7}$ cycloalkyl, 3- to 7-membered saturated heterocyclyl, cyano, and azide;
Q is optionally-substituted imidazole group;
$R^{1A}$, $R^{1B}$, $R^{1C}$, and $R^{1D}$ are each independently hydrogen atom, halogen atom, azide, or cyano, provided that all of $R^{1A}$, $R^{1B}$, $R^{1C}$, and $R^{1D}$ are not hydrogen atom;
$R^{2A}$ and $R^{2B}$ are each independently hydrogen atom or $C_{1-6}$ alkyl;
$R^{3A}$, $R^{3B}$, $R^{3C}$, and $R^{3D}$ are each independently hydrogen atom, halogen atom, hydroxy, $C_{1-6}$ alkyl, $C_{1-6}$ alkoxy, —$CO_2R^4$, —$NR^5R^6$, or —$NR^7COR^8$, or any two of $R^{3A}$, $R^{3B}$, $R^{3C}$, and $R^{3D}$ may be taken together at the common carbon atom to which they are attached to form =O;
$R^4$ and $R^8$ are each independently $C_{1-3}$ alkyl, and
$R^5$, $R^6$, and $R^7$ are each independently hydrogen atom or $C_{1-3}$ alkyl, or when $R^5$ and $R^6$ are both $C_{1-3}$ alkyl, they may be combined with the nitrogen atom to which they are attached to form 3- to 6-membered nitrogen-containing saturated heterocyclyl,
comprising the following step:
C1) reacting a compound of Formula (1a):

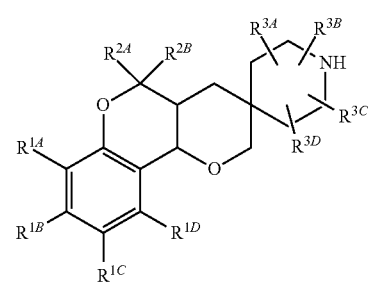

(1a)

or a pharmaceutically acceptable salt thereof,
wherein $R^{1A}$, $R^{1B}$, $R^{1C}$, $R^{1D}$, $R^{2A}$, $R^{2B}$, $R^{3A}$, $R^{3B}$, $R^{3C}$, and $R^{3D}$ are as defined above;
with a compound of Formula (4a):

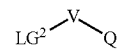

(4a)

wherein:
LG² is a leaving group; and
V and Q are as defined above;
to give the compound of Formula (4b) above.

5. The method of claim 4 wherein the compound of Formula (4b) or a pharmaceutically acceptable salt thereof is at least one selected from the group consisting of:
(4'aS,10'bS)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran];
(4'aR,10'bR)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran];
(4'aR,10'bR)-8'-chloro-1-[2-(1H-imidazol-1-yl)ethyl]-5',5'-dimethyl-4'a,10'b-dihydro-2'H,4'H,5'H-spiro[piperidine-4,3'-pyrano[3,2-c][1]benzopyran];

(4'aS,10'bS)-8'-chloro-1-[2-(1H-imidazol-1-yl)
ethyl]-5',5'-dimethyl-4'a,10'b-dihydro-2'H,4'H,
5'H-spiro[piperidine-4,3'-pyrano[3,2-c][1]benzo-
pyran];

(4'aS,10'bS)-9'-fluoro-5',5'-dimethyl-1-[2-(2-
methyl-1H-imidazol-1-yl)ethyl]-4'a,10'b-dihydro-
2'H,4'H,5'H-spiro[piperidine-4,3'-pyrano[3,2-c]
[1]benzopyran]; and (4'aR,10'bR)-9'-fluoro-5',5'-dimethyl-1-[2-(2-
methyl-1H-imidazol-1-yl)ethyl]-4'a,10'b-dihydro-
2'H,4'H,5'H-spiro[piperidine-4,3'-pyrano[3,2-c]
[1]benzopyran].

6. A process for preparing a compound of Formula (3b):

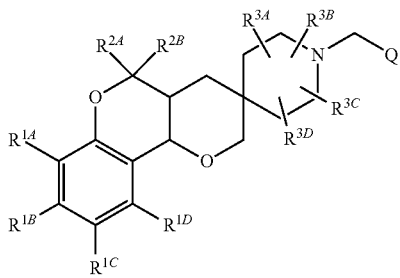

(3b)

or a pharmaceutically acceptable salt thereof,
wherein:
Q is optionally-substituted imidazole group;
$R^{1A}$, $R^{1B}$, $R^{1C}$, and $R^{1D}$ are each independently hydrogen atom, halogen atom, azide, or cyano, provided that all of $R^{1A}$, $R^{1B}$, $R^{1C}$, and $R^{1D}$ are not hydrogen atom;
$R^{2A}$ and $R^{2B}$ are each independently hydrogen atom or $C_{1-6}$ alkyl;
$R^{3A}$, $R^{3B}$, $R^{3C}$, and $R^{3D}$ are each independently hydrogen atom, halogen atom, hydroxy, $C_{1-6}$ alkyl, $C_{1-6}$ alkoxy, —$CO_2R^4$, —$NR^5R^6$, or —$NR^7COR^8$, or any two of $R^{3A}$, $R^{3B}$, $R^{3C}$, and $R^{3D}$ may be taken together at the common carbon atom to which they are attached to form =O;
$R^4$ and $R^8$ are each independently $C_{1-3}$ alkyl, and $R^5$, $R^6$, and $R^7$ are each independently hydrogen atom or $C_{1-3}$ alkyl, or when $R^5$ and $R^6$ are both $C_{1-3}$ alkyl, they may be combined with the nitrogen atom to which they are attached to form 3- to 6-membered nitrogen-containing saturated heterocyclyl,
comprising the following step:
D1) reacting a compound of Formula (1a):

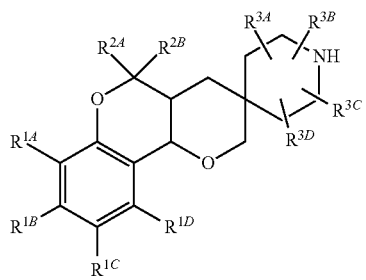

(1a)

or a pharmaceutically acceptable salt thereof, wherein $R^{1A}$, $R^{1B}$, $R^{1C}$, $R^{1D}$, $R^{2A}$, $R^{2B}$, $R^{3A}$, $R^{3B}$, $R^{3C}$, and $R^{3D}$ are as defined above;
with a compound of Formula (3a):

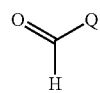

(3a)

wherein Q is as defined above;
and reducing to give the compound of Formula (3b) above.

7. The method of claim 6 wherein the compound of Formula (3b) or a pharmaceutically acceptable salt thereof is at least one selected from the group consisting of:
(4'aS,10'bS)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran]; and
(4'aR,10'bR)-8'-chloro-5',5'-dimethyl-1-[(4-methyl-1H-imidazol-5-yl)methyl]-4'a,10'b-dihydro-2'H,4'H,5'H-spiro[piperidine-4,3'-pyrano[3,2-c][1]benzopyran].

8. A process for preparing a compound of Formula (1c):

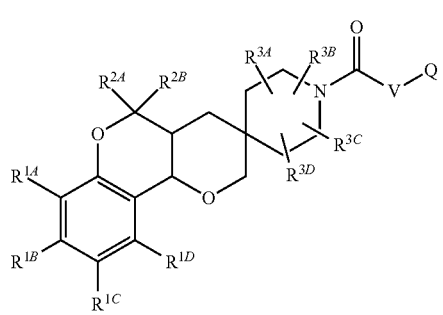

(1c)

or a pharmaceutically acceptable salt thereof,
wherein:
V is $C_{1-6}$ alkylene which may be substituted with 1 to 3 substituents selected independently from the group consisting of fluorine atom, hydroxy, $C_{1-6}$ alkoxy, $C_{3-7}$ cycloalkyl, 3- to 7-membered saturated heterocyclyl, cyano, and azide;
Q is optionally-substituted imidazole group;
$R^{1A}$, $R^{1B}$, $R^{1C}$, and $R^{1D}$ are each independently hydrogen atom, halogen atom, azide, or cyano, provided that all of $R^{1A}$, $R^{1B}$, $R^{1C}$, and $R^{1D}$ are not hydrogen atom;
$R^{2A}$ and $R^{2B}$ are each independently hydrogen atom or $C_{1-6}$ alkyl;
$R^{3A}$, $R^{3B}$, $R^{3C}$, and $R^{3D}$ are each independently hydrogen atom, halogen atom, hydroxy, $C_{1-6}$ alkyl, $C_{1-6}$ alkoxy, —$CO_2R^4$, —$NR^5R^6$, or —$NR^7COR^8$, or any two of $R^{3A}$, $R^{3B}$, $R^{3C}$, and $R^{3D}$ may be taken together at the common carbon atom to which they are attached to form =O;
$R^4$ and $R^8$ are each independently $C_{1-3}$ alkyl, and $R^5$, $R^6$, and $R^7$ are each independently hydrogen atom or $C_{1-3}$ alkyl, or when $R^5$ and $R^6$ are both $C_{1-3}$ alkyl, they may be combined with the nitrogen atom to which they are attached to form 3- to 6-membered nitrogen-containing saturated heterocyclyl, provided that the following compounds of formulae (Z-1) and (Z-2):

(Z-1)

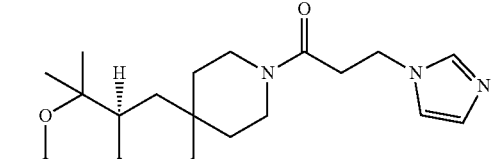

(Z-2)

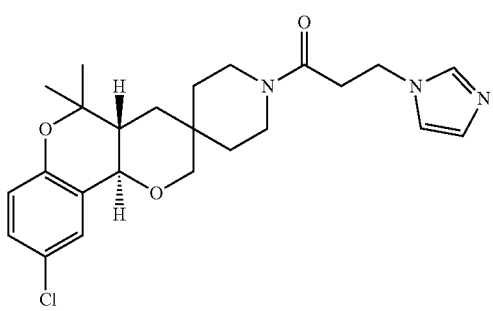

are excluded;
comprising the following steps:
E1) reacting a compound of Formula (1a):

(1a)

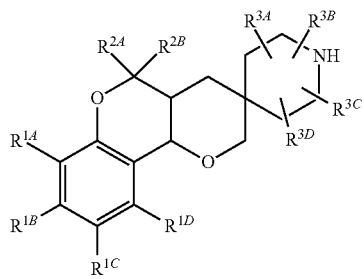

or a pharmaceutically acceptable salt thereof,
wherein $R^{1A}$, $R^{1B}$, $R^{1C}$, $R^{1D}$, $R^{2A}$, $R^{2B}$, $R^{3A}$, $R^{3B}$, $R^{3C}$, and $R^{3D}$ are as defined above;
with a compound of Formula (2a):

(2a)

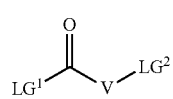

wherein:
V is as defined above;
$LG^1$ is a leaving group; and
$LG^2$ is a leaving group;

to give a compound of Formula (2b):

(2b)

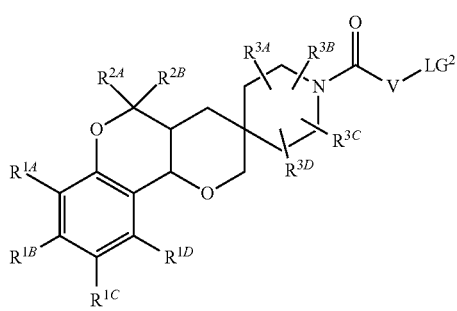

wherein V, $LG^2$, $R^{1A}$, $R^{1B}$, $R^{1C}$, $R^{1D}$, $R^{2A}$, $R^{2B}$, $R^{3A}$, $R^{3B}$, $R^{3C}$, and $R^{3D}$ are as defined above; and E2) reacting a compound of Formula (2b) above with an imidazole derivate (QH) to give the compound of Formula (1c) above.

9. A process for preparing a compound of Formula (1c):

(1c)

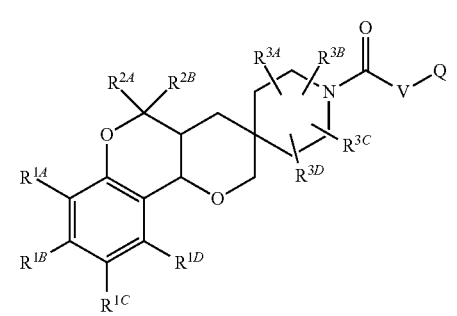

or a pharmaceutically acceptable salt thereof,
wherein:
V is $C_{1-6}$ alkylene which may be substituted with 1 to 3 substituents selected independently from the group consisting of fluorine atom, hydroxy, $C_{1-6}$ alkoxy, $C_{3-7}$ cycloalkyl, 3- to 7-membered saturated heterocyclyl, cyano, and azide;
Q is optionally-substituted imidazole group;
$R^{1A}$, $R^{1B}$, $R^{1C}$, and $R^{1D}$ are each independently hydrogen atom, halogen atom, azide, or cyano, provided that all of $R^{1A}$, $R^{1B}$, $R^{1C}$, and $R^{1D}$ are not hydrogen atom;
$R^{2A}$ and $R^{2B}$ are each independently hydrogen atom or $C_{1-6}$ alkyl;
$R^{3A}$, $R^{3B}$, $R^{3C}$, and $R^{3D}$ are each independently hydrogen atom, halogen atom, hydroxy, $C_{1-6}$ alkyl, $C_{1-6}$ alkoxy, —$CO_2R^4$, —$NR^5R^6$, or —$NR^7COR^8$, or any two of $R^{3A}$, $R^{3B}$, $R^{3C}$, and $R^{3D}$ may be taken together at the common carbon atom to which they are attached to form =O;
$R^4$ and $R^8$ are each independently $C_{1-3}$ alkyl, and $R^5$, $R^6$, and $R^7$ are each independently hydrogen atom or $C_{1-3}$ alkyl, or when $R^5$ and $R^6$ are both $C_{1-3}$ alkyl, they may be combined with the nitrogen atom to which they are attached to form 3- to 6-membered nitrogen-containing saturated heterocyclyl,
provided that the following compounds of formulae (Z-1) and (Z-2):

(Z-1)
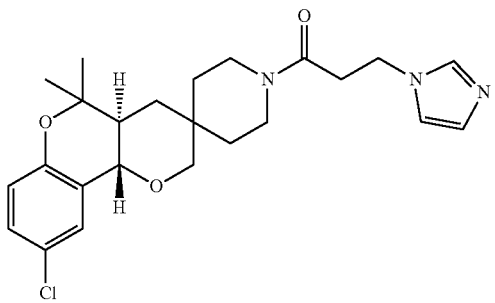
(Z-2)
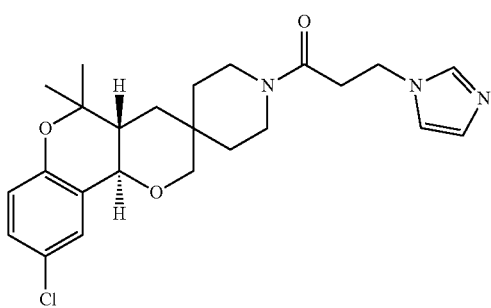
are excluded;
comprising the following step:
F1) reacting a compound of Formula (1a):
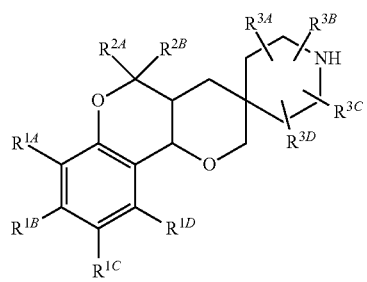
(1a)
or a pharmaceutically acceptable salt thereof,
wherein $R^{1A}$, $R^{1B}$, $R^{1C}$, $R^{1D}$, $R^{2A}$, $R^{2B}$, $R^{3A}$, $R^{3B}$, $R^{3C}$, and $R^{3D}$ are defined above;
with a compound of Formula (1b):
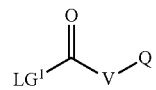
(1b)
wherein:
V and Q are as defined above; and
$LG^1$ is a leaving group;
to give a compound of Formula (1c) above.
* * * * *